(12) United States Patent
Walz et al.

(10) Patent No.: US 11,744,697 B2
(45) Date of Patent: Sep. 5, 2023

(54) ACCOMMODATING INTRAOCULAR LENSES WITH TORIC SURFACE

(71) Applicant: Alcon Inc., Fribourg (CH)

(72) Inventors: Andrew R. Walz, Portola Valley, CA (US); Robert Angelopoulos, San Jose, CA (US); Nathan Lewis, San Jose, CA (US)

(73) Assignee: Alcon Inc., Fribourg (CH)

( * ) Notice: Subject to any disclaimer, the term of this patent is extended or adjusted under 35 U.S.C. 154(b) by 205 days.

(21) Appl. No.: 17/060,919

(22) Filed: Oct. 1, 2020

(65) Prior Publication Data

US 2021/0100652 A1 Apr. 8, 2021

Related U.S. Application Data

(60) Provisional application No. 62/911,020, filed on Oct. 4, 2019.

(51) Int. Cl.
*A61F 2/16* (2006.01)

(52) U.S. Cl.
CPC .......... *A61F 2/1635* (2013.01); *A61F 2/1645* (2015.04); *A61F 2/1648* (2013.01); *A61F 2/164* (2015.04); *A61F 2002/1681* (2013.01); *A61F 2002/1682* (2015.04); *A61F 2250/0036* (2013.01)

(58) Field of Classification Search
None
See application file for complete search history.

(56) References Cited

U.S. PATENT DOCUMENTS

| | | |
|---|---|---|
| 2010/0179653 A1 | 7/2010 | Argento et al. |
| 2016/0008126 A1 | 1/2016 | Salahieh et al. |
| 2016/0058552 A1* | 3/2016 | Argal .................. A61F 2/161 623/6.4 |
| 2016/0106534 A1 | 4/2016 | Deboer et al. |
| 2018/0177589 A1* | 6/2018 | Argento ............. A61F 2/1635 |
| 2018/0256315 A1 | 9/2018 | Hildebrand et al. |
| 2019/0269500 A1 | 9/2019 | De Juan, Jr. et al. |

FOREIGN PATENT DOCUMENTS

WO  WO 2021/067575  4/2021

* cited by examiner

*Primary Examiner* — Leslie Lopez
(74) *Attorney, Agent, or Firm* — Levine Bagade Han LLP

(57) ABSTRACT

Disclosed are toric accommodating intraocular lenses. In one embodiment, a toric accommodating intraocular lens comprises an anterior element and a posterior element. The anterior element can comprise an anterior optical surface. The posterior element can comprise a posterior optical surface. A fluid-filled optic fluid chamber can be defined in between the anterior element and the posterior element. The toric accommodating intraocular lens can be configured to correct for corneal astigmatism, spherical aberration, or a combination thereof.

20 Claims, 8 Drawing Sheets

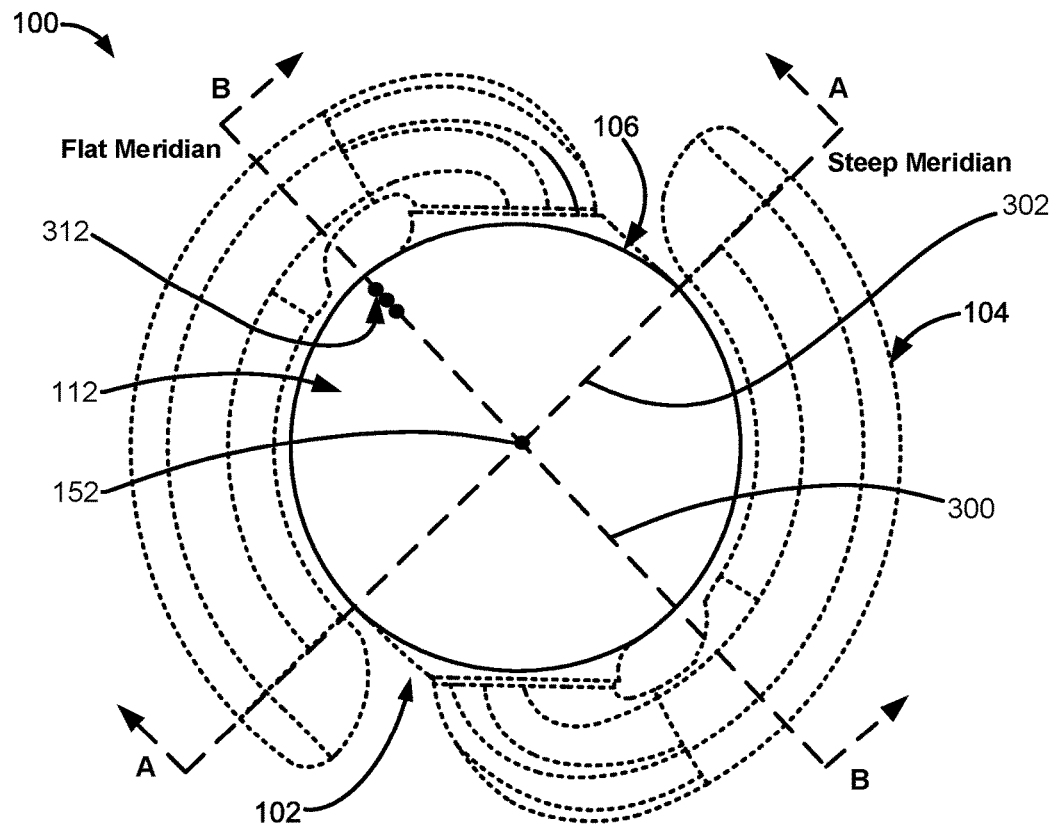
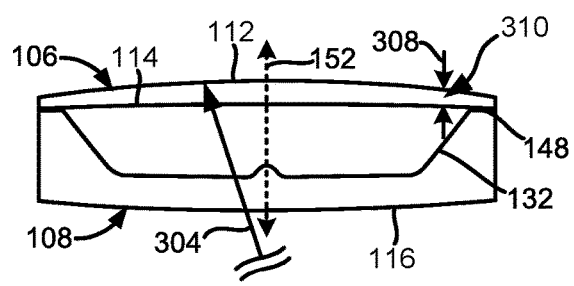 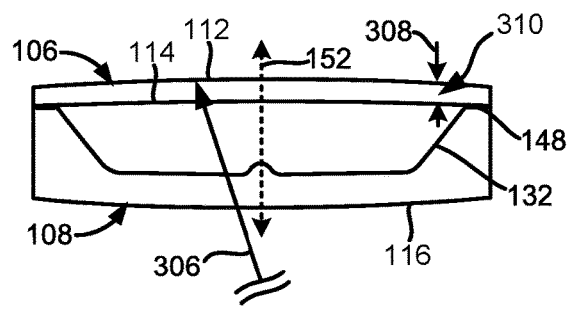
FIG. 3A
FIG. 3B  FIG. 3C

ACCOMMODATING INTRAOCULAR LENSES WITH TORIC SURFACE

CROSS-REFERENCE TO RELATED APPLICATION

This application claims the benefit of U.S. Provisional Application No. 62/911,020 filed on Oct. 4, 2019, the entirety of which is incorporated herein by reference.

TECHNICAL FIELD

The present disclosure relates generally to the field of intraocular lenses, and, more specifically, to an accommodating intraocular lens with a toric lens surface.

BACKGROUND

A cataract is a condition involving the clouding over of the normally clear lens of a patient's eye. Cataracts occur as a result of aging, hereditary factors, trauma, inflammation, metabolic disorders, or exposure to radiation. Age-related cataract is the most common type of cataracts. In treating a cataract, the surgeon removes the crystalline lens matrix from the patient's lens capsule and replaces it with an intraocular lens (IOL). Traditional IOLs provide one or more selected focal lengths that allow the patient to have distance vision. However, after cataract surgery, patients with traditional IOLs often require glasses or other corrective eyewear for certain activities since the eye can no longer undertake accommodation (or change its optical power) to maintain a clear image of an object or focus on an object as its distance varies.

Newer IOL such as accommodating IOLs, allow the eye to regain at least some focusing ability. Accommodating IOLs (AIOLs) use forces available in the eye to change some portion of the optical system in order to refocus the eye on distant or near targets. This can be considered dynamic defocus and a lower order aberration. Examples of AIOLs are discussed in the following U.S. patent publications: U.S. Pat. Pub. No. 2018/0256315; U.S. Pat. Pub. No. 2018/0153682; and U.S. Pat. Pub. No. 2017/0049561 and in the following issued U.S. patents: U.S. Pat. Nos. 10,299,913; 10,195,020; and 8,968,396, the contents of which are incorporated herein by reference in their entireties.

Besides lower-order aberrations, higher-order aberrations can also create visual disturbances and are also commonly corrected with artificial lenses. These aberrations can include cylindrical astigmatism and spherical aberration. Cylindrical astigmatism is generally developed in the cornea naturally and a large proportion of patients with preexisting cataracts also have some degree of astigmatism. While toric IOLs have been used to correct astigmatism at the time of cataract surgery, such toric IOLs suffer from the same drawbacks as traditional IOLs in that they do not provide for accommodation.

Moreover, another difficulty faced by all toric lens makers is that such lenses have different powers in different meridians so maintaining the cylinder orientation of the lens post-implantation is crucial. Such a difficulty is made even more challenging when astigmatism correction is attempted along with accommodation or along with accommodation and spherical aberration correction.

Therefore, a solution is needed which addresses the above shortcomings and disadvantages of traditional IOLs and toric IOLs. Such a solution should not be overly complicated and be cost-effective to manufacture.

SUMMARY

Disclosed herein are accommodating intraocular lenses for correcting corneal astigmatism and accommodating intraocular lenses for correcting both corneal stigmatism and spherical aberration. In one embodiment, a toric accommodating intraocular lens is disclosed comprising an optic portion comprising an anterior element and a posterior element. The anterior element can comprise an anterior optical surface. The posterior element can comprise a posterior optical surface. A fluid-filled optic fluid chamber can be defined in between the anterior element and the posterior element. At least one of the anterior optical surface and the posterior optical surface can be shaped such that a radius of curvature of the at least one of the anterior optical surface and the posterior optical surface differs along different optical surface meridians.

In some embodiments, the radius of curvature of the posterior optical surface can vary periodically around the posterior optical surface. In certain embodiments, the radius of curvature varies periodically (e.g., sinusoidally) around the posterior optical surface.

The posterior element can further comprise a posterior inner surface. The posterior inner surface can be a surface of the posterior element facing the optic fluid chamber. The posterior inner surface can be rotationally symmetric or substantially rotationally symmetric. The posterior inner surface can be rotationally symmetric when the radius of curvature of the posterior inner surface is the same or substantially the same along all surface meridians.

The posterior element can also have a posterior element thickness as measured from the posterior optical surface to the posterior inner surface. The posterior element thickness can vary periodically around the posterior element such that the posterior element thickness differs along different optical surface meridians. The posterior element thickness can vary sinusoidally around the posterior element.

In some embodiments, the radius of curvature of the anterior optical surface can vary periodically around the anterior optical surface. The radius of curvature of the anterior optical surface can vary periodically around the anterior optical surface when the radius of curvature along one optical surface meridian differs from the radius of curvature of the anterior optical surface along another optical surface meridian. In certain embodiments, the radius of curvature varies periodically (e.g., sinusoidally) around the anterior optical surface.

The anterior element can further comprise an anterior inner surface. The anterior inner surface can be a surface of the anterior element facing the optic fluid chamber. In some embodiments, at least part of the anterior inner surface and the posterior inner surface can serve as chamber walls of the optic fluid chamber. The anterior inner surface can be rotationally symmetric or substantially rotationally symmetric. The anterior inner surface can be rotationally symmetric when the radius of curvature of the anterior inner surface is the same or substantially the same along all surface meridians.

The anterior element can also have an anterior element thickness as measured from the anterior optical surface to the anterior inner surface. The anterior element thickness can vary periodically around the anterior element such that the anterior element thickness differs along different optical surface meridians. The anterior element thickness can vary sinusoidally around the anterior element.

At least one of the anterior optical surface and the posterior optical surface can comprise a flat meridian and a steep meridian oriented substantially perpendicular to the flat meridian. The radius of curvature is the least along the steep meridian and the radius of curvature is the greatest along the flat meridian.

A refractive dioptric power of an external optical surface (either the posterior optical surface or the anterior optical surface) of the toric accommodating intraocular lens can be the greatest along a steep meridian of the external optical surface and the refractive dioptric power of the external optical surface can be the least along a flat meridian of the same external optical surface. The steep meridian and the flat meridian can be considered the principal meridians of the lens. The flat meridian can also be referred to as the cylinder axis or simply "axis" of a toric lens.

For example, the radius of curvature of the posterior optical surface can be the least along the steep meridian of the posterior optical surface. The radius of curvature of the posterior optical surface can be the greatest along the flat meridian of the same posterior optical surface. Moreover, the posterior element thickness can be the greatest (or thickest) along the flat meridian. The posterior element thickness can be the least (or thinnest) along the steep meridian.

Also, for example, the radius of curvature of the anterior optical surface can be the least along the steep meridian of the anterior optical surface. The radius of curvature of the anterior optical surface can be the greatest along the flat meridian of the same anterior optical surface. Moreover, the anterior element thickness can be the greatest (or thickest) along the flat meridian. The anterior element thickness can be the least (or thinnest) along the steep meridian.

The optic portion can have a base power or base spherical power. The base power of the optic portion can be configured to change based on an internal fluid pressure within the fluid-filled optic fluid chamber. The base power of the optic portion can be configured to increase or decrease as fluid enters or exits the optic fluid chamber. The optic portion can be configured to change shape in response to fluid entering or exiting the optic fluid chamber. In certain embodiments, the anterior element of the optic portion can be configured to change shape in response to the fluid entering or exiting the optic fluid chamber. In other embodiments, the posterior element of the optic portion can be configured to change shape in response to the fluid entering or exiting the optic fluid chamber. In further embodiments, both the anterior element and the posterior element of the optic portion can be configured to change shape in response to the fluid entering or exiting the optic fluid chamber.

The base power of the optic portion can be configured to change in response to the shape change undertaken by the shape-changing optic portion (e.g., the anterior element, the posterior element, or a combination thereof). The shape-changing optic portion is configured to change shape in response to a physiologic muscle movement (e.g., ciliary muscle movement) undertaken by a patient when the toric accommodating intraocular lens is implanted within an eye of the patient.

In some embodiments, the toric accommodating intraocular lens can comprise one or more haptics coupled to and extending from the optic portion. Each of the one or more haptics can comprise a haptic fluid chamber within the haptic. The base power of the optic portion can be configured to increase as fluid enters the optic fluid chamber from the haptic fluid chamber(s). The base power of the optic portion can be configured to decrease as fluid exits or is drawn out of the optic fluid chamber into the haptic fluid chamber(s).

The optic fluid chamber can be in fluid communication with or fluidly connected to the haptic fluid chamber(s). The optic fluid chamber can be in fluid communication with a haptic fluid chamber through a pair of fluid channels. The fluid channels can be conduits or passageways fluidly connecting the optic fluid chamber to the haptic fluid chamber. The pair of fluid channels can be spaced apart from one another. For example, the pair of fluid channels can be spaced apart between about 0.1 mm to about 1.0 mm.

In some embodiments, the pair of fluid channels can be defined and extend through part of the optic portion. More specifically, the pair of fluid channels can be defined and extend through the posterior element.

The one or more haptics can be coupled to the optic portion at a haptic-optic interface. The one or more haptics can be coupled to the optic portion at a reinforced portion along the optic portion. The reinforced portion can be part of the haptic-optic interface. The pair of fluid channels can be defined or formed within part of the reinforced portion.

In some embodiments, the toric accommodating intraocular lens can comprise two haptics coupled to and extending from the optic portion. The first haptic can comprise a first haptic fluid chamber within the first haptic. The second haptic can comprise a second haptic fluid chamber within the second haptic. The first haptic can be coupled to the optic portion at a first haptic-optic interface and the second haptic can be coupled to the optic portion at a second haptic-optic interface.

In these embodiments, the optic fluid chamber can be in fluid communication with both the first haptic fluid chamber and the second haptic fluid chamber. The optic fluid chamber can be in fluid communication with the first haptic fluid chamber through a first pair of fluid channels. The optic fluid chamber can be in fluid communication with the second haptic fluid chamber through a second pair of fluid channels.

The first pair of fluid channels can be spaced apart from one another. The first pair of fluid channels can be spaced apart between about 0.1 mm to about 1.0 mm. The second pair of fluid channels can be spaced apart from one another. The second pair of fluid channels can be spaced apart between about 0.1 mm to about 1.0 mm.

The first pair of fluid channels and the second pair of fluid channels can be defined and extend through part of the optic portion. The first pair of fluid channels and the second pair of fluid channels can be defined and extend through the posterior element.

The optic portion can also comprise a first reinforced portion and a second reinforced portion substantially on opposing sides of the optic portion or substantially diametrically opposed to one another. The first pair of fluid channels can be defined or formed within the first reinforced portion. The second pair of fluid channels can be defined or formed within the second reinforced portion.

The first pair of fluid channels can terminate at a first pair of apertures defined within the optic portion. The first pair of fluid channels can terminate at a first pair of apertures defined within the posterior element. The first pair of apertures can be spaced apart between about 0.1 mm to about 1.0 mm. The second pair of fluid channels can terminate at a second pair of apertures defined within the optic portion. The second pair of fluid channels can terminate at a second pair of apertures within the posterior element. The second pair of apertures can be spaced apart between about 0.1 mm to about 1.0 mm.

In some embodiments, the first pair of fluid channels and the second pair of fluid channels can be positioned substantially on opposite sides of the optic portion. The first pair of fluid channels can be positioned substantially diametrically opposed to the second pair of fluid channels.

In these embodiments, the first pair of apertures and the second pair of apertures can be positioned substantially on opposite sides of the optic portion. The first pair of apertures can be positioned substantially diametrically opposed to the second pair of apertures.

As previously discussed, the base power or base spherical power of the optic portion can be configured to change based on the internal fluid pressure within the fluid-filled optic fluid chamber. The toric accommodating intraocular lens can also have a cylinder power.

The cylinder power of the toric accommodating intraocular lens can be the dioptric power of the toric accommodating intraocular lens along the steep meridian. The cylinder power is often expressed as a difference in dioptric power (e.g., +1.0 D or +3.0 D) provided by the steep curvature of the toric lens along the steep meridian.

In some embodiments, the toric accommodating intraocular lens can have a cylinder power of between about +0.75 D to about +6.00 D. For example, the toric accommodating intraocular lens can have a cylinder power of about +0.75 D, +1.50 D, +2.25 D, +3.00 D, +3.75 D, +4.50 D, +5.25 D, or +6.00 D. In some embodiments, the toric accommodating intraocular lens can have a cylinder power of about +0.75 D (referred to as a low cylinder). In other embodiments, the toric accommodating intraocular lens can have a cylinder power of about +6.0 D (referred to as a high cylinder).

One technical problem faced by the applicants is how to introduce cylindricity or a toric surface to an accommodating intraocular lens such that the cylinder power of the accommodating intraocular lens remains substantially unchanged or stable across all base power changes throughout accommodation or disaccommodation of the lens (for example, a base power change of between about ±1.0 and about ±10.0).

One solution discovered by the applicants is to vary a radius of curvature of the external optical surface (e.g., the posterior optical surface or the anterior optical surface) while keeping an inner surface (e.g., the posterior inner surface or the anterior inner surface) opposite the external optical surface rotationally symmetric. Another solution provided by the present disclosure is to orient the flat meridian of the external optical surface at an oblique angle with respect to a midline substantially bisecting the optic portion. Orienting the flat meridian will be discussed in more detail in the following sections.

By designing the toric accommodating intraocular lens in this manner, the cylinder power of the optic portion can remain substantially unchanged or stable throughout the change in base power of the optic portion in response to changes in the fluid pressure within the fluid-filled optic fluid chamber. For example, the relative refractive dioptric power between the steep meridian and the flat meridian can remain substantially unchanged or stable when the base power of the optic portion changes throughout accommodation and disaccommodation.

The toric accommodating intraocular lens can also have a cylinder orientation. Cylinder orientation can refer to an orientation or positioning of the meridians of the lens. For example, cylinder orientation can refer to the orientation or positioning of the flat meridian (i.e., the cylinder axis), the steep meridian, or a combination thereof relative to other components of the lens. Cylinder orientation can also refer to the orientation or positioning of one meridian relative to another meridian.

Another technical problem faced by the applicants is how to keep the cylinder orientation of a toric accommodating intraocular lens substantially unchanged or fixed across all base power changes throughout accommodation or disaccommodation of the lens. A toric intraocular lens having a cylinder orientation which changes or shifts significantly when implanted within the eye is at best without benefit (or has no astigmatic correcting effects) and, at worst, can adversely affect a patient's vision (e.g., induce astigmatism in another meridian).

One solution discovered by the applicants is to orient the flat meridian of the toric accommodating intraocular lens at an oblique angle to a midline substantially bisecting the optic portion. By designing the toric accommodating intraocular lens in this manner, the cylinder orientation of the optic portion can remain substantially unchanged throughout the change in base power of the optic portion in response to changes in the internal fluid pressure within the fluid-filled optic fluid chamber. For example, the orientation or positioning of the flat meridian of the toric accommodating intraocular lens can remain substantially unchanged or fixed relative to the corneal astigmatism axis of the eye when the base power of the optic portion changes throughout accommodation and disaccommodation.

In some embodiments, the oblique angle can be a clockwise rotational angle with respect to the midline. For example, the oblique angle can be a clockwise rotational angle of between about 30 degrees and 60 degrees. More specifically, the flat meridian can be oriented at a clockwise rotational angle of between about 30 degrees and 60 degrees with respect to the midline. In certain embodiments, the oblique angle can be a clockwise rotational angle of about 45 degrees. More specifically, the flat meridian can be oriented at a clockwise rotational angle of about 45 degrees with respect to the midline.

In some embodiments, the midline can be a line or axis that substantially bisects the optic portion or divides the optic portion in half. In these and other embodiments, the midline can substantially bisect the haptic-optic interface or extend through a midportion of the haptic-optic interface. For example, the midline can substantially bisect both a first haptic-optic interface and a second haptic-optic interface. The midline can also extend through or substantially bisect the first reinforced portion and the second reinforced portion.

As previously discussed, the optic portion can comprise at least one pair of fluid channels configured to place the fluid-filled optic fluid chamber in fluid communication with a haptic fluid chamber. The midline can extend in between the pair of fluid channels or substantially bisect a part of the optic portion separating the pair of fluid channels. In some embodiments, the midline can extend in between the pair of apertures or bisect a part of the optic portion separating the pair of apertures disposed at the end of the pair of fluid channels. For example, the optic portion can comprise a first pair of fluid channels and a second pair of fluid channels, the midline can extend in between or substantially bisect a part of the optic portion separating the first pair of fluid channels and the second pair of fluid channels.

In some embodiments, the anterior element can be configured such that the anterior optical surface is aspheric or changes shape from a spherical surface configuration to an aspherical surface configuration in response to fluid entering the fluid-filled optic fluid chamber. In some embodiments, the fluid can enter the fluid-filled optic fluid chamber from one or more haptic fluid chambers of haptics coupled to the optic portion.

In other embodiments, the posterior element can be configured such that the posterior optical surface is aspheric or changes shape from a spherical surface configuration to an aspherical surface configuration in response to fluid entering the fluid-filled optic fluid chamber. An aspherical surface configuration can correct for high order aberrations such as spherical aberration.

An additional technical problem faced by the applicants is how to introduce both cylindricity/toricity and asphericity to an accommodating intraocular lens. An accommodating intraocular lens that can correct for both corneal astigmatism and spherical aberration can allow cataract patients suffering from such higher order aberrations to rely on only one pair of accommodating intraocular lenses to correct for such aberrations.

One solution discovered by the applicants is to separate the external optical surface configured to change into the aspherical surface configuration from the external optical surface having the toric lens surface. For example, the accommodating intraocular lens can be configured such that the aspheric optical surface is on an opposite lens element from the lens element having the toric optical surface.

In some embodiments, the posterior element can be shaped such that the radius of curvature of the posterior optical surface differs along different optical surface meridians and the anterior element can be an aspherical surface.

In other embodiments, the anterior element can be shaped such that the radius of curvature of the anterior optical surface differs along different optical surface meridians and the posterior element is an aspherical surface.

Similar to the cylinder power and cylinder orientation, the asphericity of the external optical surface can be maintained or remain stable across certain or all base power changes throughout accommodation or disaccommodation.

In some embodiments, the external optical surface (either the anterior optical surface or the posterior optical surface) can be stressed into the aspherical surface configuration as fluid enters the fluid-filled optic fluid chamber defined by the anterior element and the posterior element. The external optical surface can be stressed into the aspherical surface configuration as a center or central portion of an optic element (either the anterior element or the posterior element) flexes or bulges out further than an outer periphery of the optic element which is held down by adhesive or an adhesive layer.

The adhesive or adhesive layer can bond or otherwise join the anterior element to the posterior element. The adhesive or adhesive layer can be substantially annular-shaped.

In these and other embodiments, the optic element can have a thickness at its center or central portion that is greater than a thickness at its periphery. This difference in thickness can also contribute to the external optical surface changing its shape from the spherical surface configuration to the aspherical surface configuration as fluid enters the fluid-filled optic fluid chamber. For example, the anterior element can have a thickness at its center or central portion that is great than a thickness at the periphery of the anterior element. This difference in thickness can enable the anterior optical surface to change shape from the spherical surface configuration to the aspherical surface configuration as the internal fluid pressure within the optic fluid chamber increases.

BRIEF DESCRIPTION OF THE DRAWINGS

FIG. 3A illustrates a top plan view of an anterior element of an embodiment of the toric accommodating intraocular lens.

FIG. 3B illustrates a sectional view of the anterior element taken along cross-section A-A of FIG. 3A.

FIG. 3C illustrates a sectional view of the anterior element taken along cross-section B-B of FIG. 3A.

DETAILED DESCRIPTION

Figure 1A:
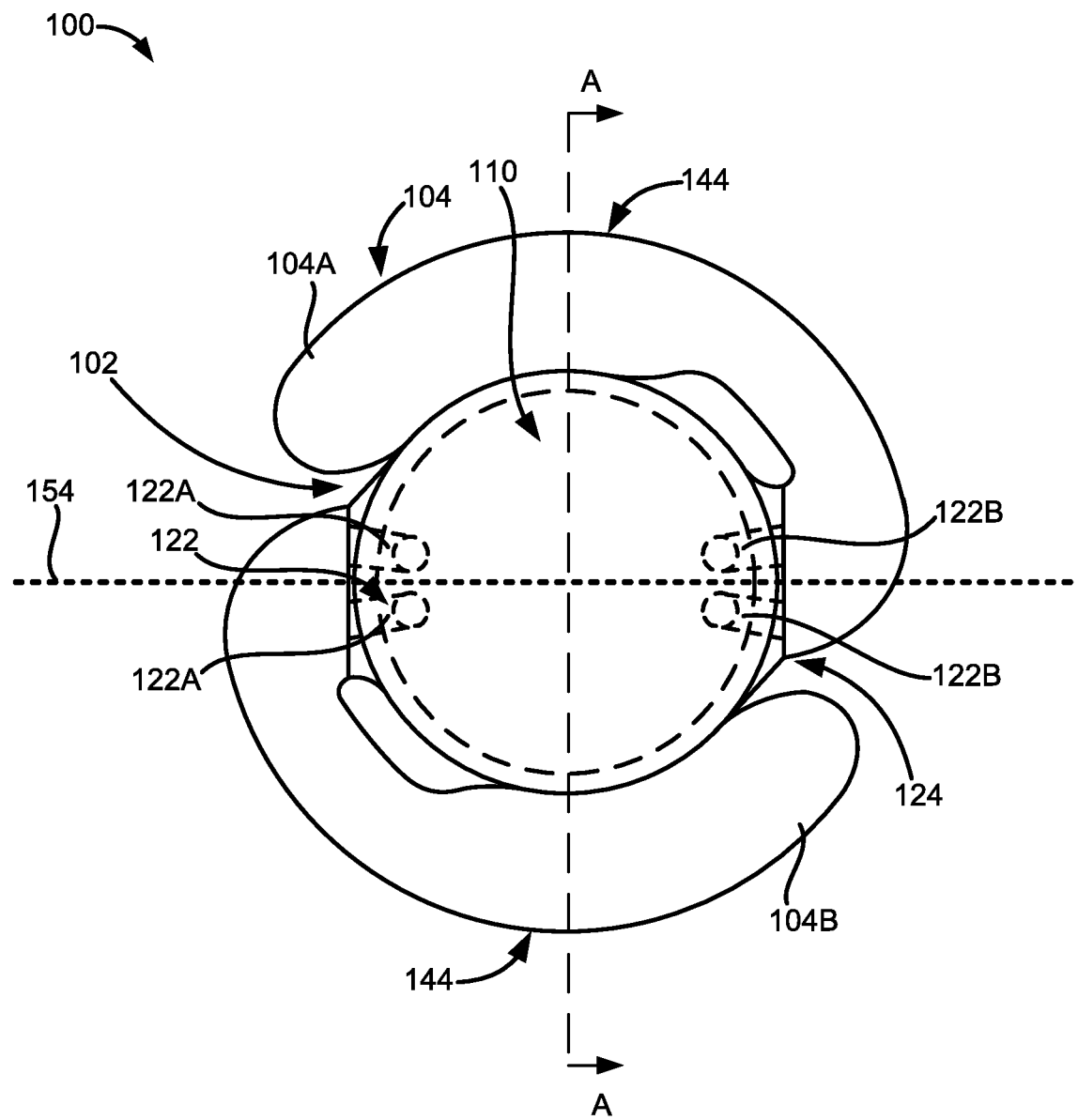
FIG. 1A illustrates a top plan view of an embodiment of a toric accommodating intraocular lens.

FIG. 1A illustrates a top plan view of an embodiment of a toric accommodating intraocular lens (AIOL) 100 for correcting corneal astigmatism, spherical aberration, or a combination thereof. The toric AIOL 100 can comprise an optic portion 102 and a peripheral portion that, in this embodiment, comprises one or more haptics 104 including a first haptic 104A and a second haptic 104B coupled to and extending peripherally from the optic portion 102. The toric AIOL 100 is configured to be positioned within a native capsular bag in which a native lens has been removed.

When implanted within the native capsular bag, the optic portion 102 can be adapted to refract light that enters the eye onto the retina. The one or more haptics 104 can be configured to engage the capsular bag and are adapted to deform in response to ciliary muscle movement (e.g., muscle relaxation, muscle contraction, or a combination thereof) in connection with capsular bag reshaping. Engagement of the haptics 104 with the capsular bag will be discussed in more detail in the following sections.

Figure 1B:
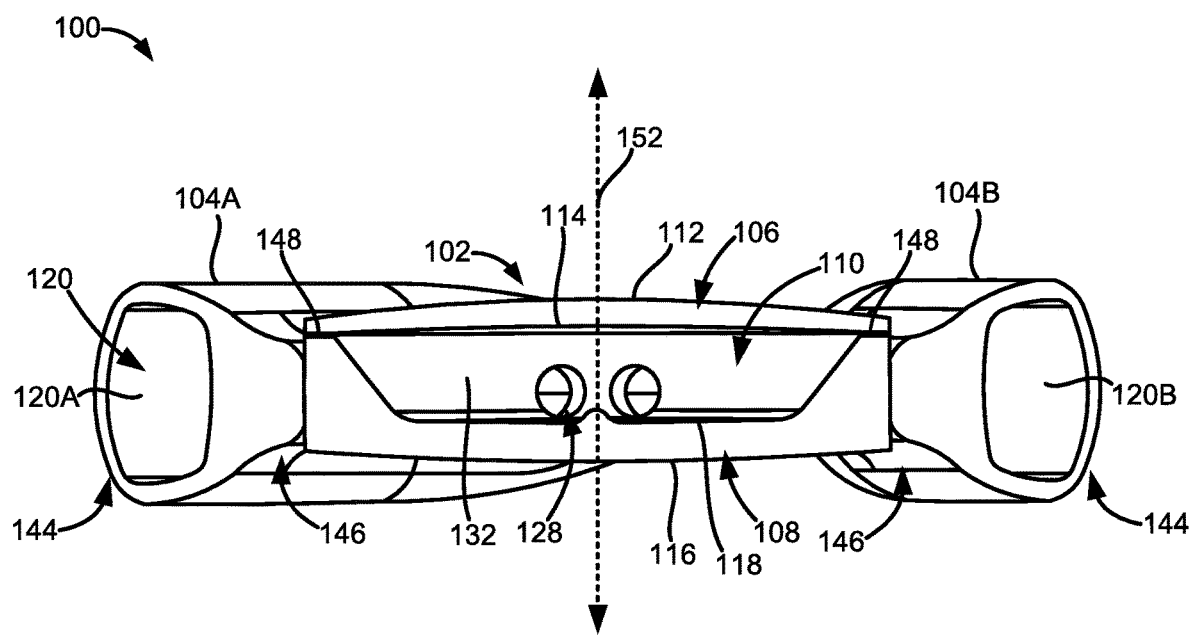
FIG. 1B illustrates a sectional view of an embodiment of the toric accommodating intraocular lens.

FIG. 1B illustrates a sectional view of an embodiment of the toric AIOL 100 as taken along cross-section A-A of FIG. 1A. As shown in FIG. 1B, the optic portion 102 can comprise an anterior element 106 and a posterior element 108. A fluid-filled optic fluid chamber 110 can be defined in between the anterior element 106 and the posterior element 108.

The anterior element 106 can comprise an anterior optical surface 112 and an anterior inner surface 114 opposite the anterior optical surface 112. The posterior element 108 can comprise a posterior optical surface 116 and a posterior inner surface 118 opposite the posterior optical surface 116.

Any of the anterior optical surface 112, the posterior optical surface 116, or a combination thereof can be considered and referred to as an external optical surface. The anterior inner surface 114 and the posterior inner surface 118 can face the optic fluid chamber 110. At least part of the anterior inner surface 114 and at least part of the posterior inner surface 118 can serve as chamber walls of the optic fluid chamber 110.

Each of the one or more haptics 104 can comprise a haptic fluid chamber 120 within the haptic 104. For example, the first haptic 104A can comprise a first haptic fluid chamber 120A within the first haptic 104A and the second haptic 104B can comprise a second haptic fluid chamber 120B within the second haptic 104B. The haptic fluid chamber 120 (e.g., any of the first haptic fluid chamber 120A, the second haptic fluid chamber 120B, or a combination thereof) can be in fluid communication with or fluidly connected to the optic fluid chamber 110.

The optic fluid chamber 110 can be in fluid communication with the one or more haptic fluid chambers 120 through a pair of fluid channels 122 (see FIG. 1A). The fluid channels 122 can be conduits or passageways fluidly connecting the optic fluid chamber 110 to the haptic fluid chamber 120. The pair of fluid channels 122 can be spaced apart from one another. For example, the pair of fluid channels 122 can be spaced apart between about 0.1 mm to about 1.0 mm. In some embodiments, each of the pair of fluid channels 122 has a diameter of between about 0.4 mm to about 0.6 mm.

In some embodiments, the pair of fluid channels 122 can be defined and extend through part of the optic portion 102. More specifically, the pair of fluid channels 122 can be defined and extend through the posterior element 108.

FIG. 1A illustrates that one or more haptics 104 can be coupled to the optic portion 102 at a haptic-optic interface 124. For example, the one or more haptics 104 can be coupled to the optic portion at a reinforced portion 126 (see FIG. 1C) along the optic portion 102. The reinforced portion 126 can be part of the haptic-optic interface 124. The pair of fluid channels 122 can be defined or formed within part of the reinforced portion 126.

The optic fluid chamber 110 can be in fluid communication with the first haptic fluid chamber 120A through a first pair of fluid channels 122A. The optic fluid chamber 110 can also be in fluid communication with the second haptic fluid chamber 120B through a second pair of fluid channels 122B.

The two fluid channels of the first pair of fluid channels 122A can be spaced apart from one another. The two fluid channels of the first pair of fluid channels 122A can be spaced apart from one another between about 0.1 mm to about 1.0 mm. The two fluid channels of the second pair of fluid channels 122B can be spaced apart from one another. The two fluid channels of the second pair of fluid channels 122B can be spaced apart from one another between about 0.1 mm to about 1.0 mm.

In some embodiments, the first pair of fluid channels 122A and the second pair of fluid channels 122B can be positioned substantially on opposite sides of the optic portion 102. The first pair of fluid channels 122A can be positioned substantially diametrically opposed to the second pair of fluid channels 122B.

The first pair of fluid channels 122A and the second pair of fluid channels 122B can be defined or extend through part of the optic portion 102. The first pair of fluid channels 122A and the second pair of fluid channels 122B can be defined or extend through the posterior element 108.

A design with two fluid channels 122 rather than one channel helps maintain dimensional stability during assembly, which can be important when assembling flexible and thin components. Additionally, it was observed through experimentation that a design with two fluid channels 122 provided better optical quality than certain one-channel designs throughout the range of accommodation. The additional stiffness of the two fluid channel design results in less deflection due to pressure changes in the fluid channels.

Figure 1C:
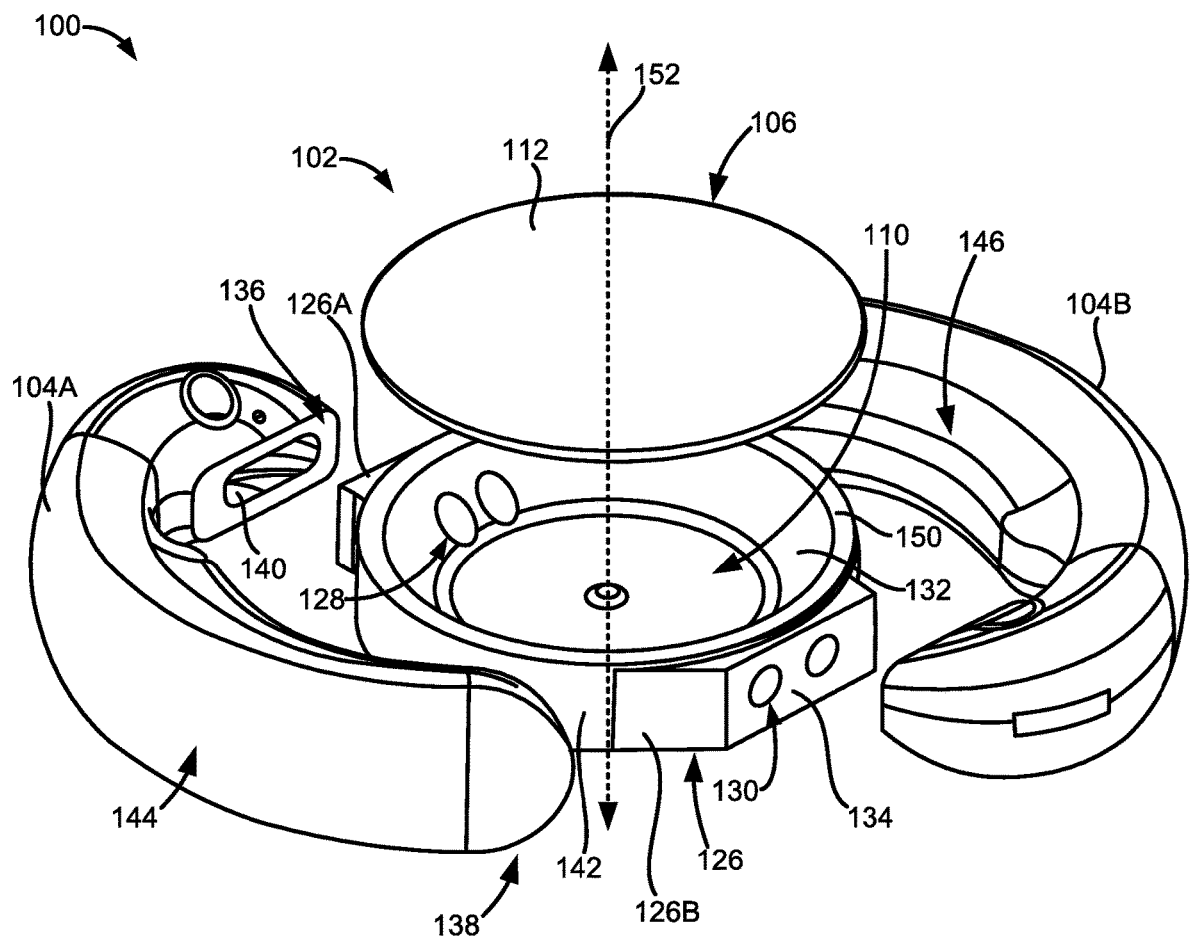
FIG. 1C illustrates an exploded view of an embodiment of the toric accommodating intraocular lens.

As shown in FIG. 1C, the optic portion 102 can comprise a first reinforced portion 126A and a second reinforced portion 126B substantially on opposing sides of the optic portion 102 or substantially diametrically opposed to one another. The first pair of fluid channels 122A can be defined or formed within the first reinforced portion 126A. The second pair of fluid channels 122B can be defined or formed within the second reinforced portion 126B.

The pair of fluid channels 122 (e.g., any of the first pair of fluid channels 122A or the second pair of fluid channels 122B) can have a pair of inner apertures 128 disposed at one end of the fluid channels 122 and another pair of outer apertures 130 disposed at the other end of the fluid channels 122. The pair of inner apertures 128 can be defined or formed on part of the posterior element 108. As shown in FIGS. 1B and 1C, the inner apertures 128 can be defined or formed on part of a raised inner surface 132 of the posterior element 108. In some embodiments, the raised inner surface 132 can be a sloped or beveled surface.

The pair of outer apertures 130 can be defined or formed on part of a protruding outer surface 134 of the posterior element 108. The protruding outer surface 134 can be part of the reinforced portion 126. The protruding outer surface 134 can also be part of the haptic-optic interface 124.

For example, FIG. 1C shows a pair of inner apertures 128 disposed at one end of the first pair of fluid channels 122A and defined along the raised inner surface 132 of the posterior element 108. FIG. 1C also shows a pair of outer apertures 130 serving as ends of the second pair of fluid channels 122B and defined along the protruding outer surface 134 of the posterior element 108. The pair of outer apertures 130 of the first pair of fluid channels 122A and the pair of inner apertures 128 of the second pair of fluid channels 122B are obscured in FIG. 1C.

The two apertures of the pair of inner apertures 128 can be spaced apart from one another between about 0.1 mm to about 1.0 mm. The two apertures of the pair of outer apertures 130 can be spaced apart from one another between about 0.1 mm to about 1.0 mm. The pair of inner apertures 128 of the first pair of fluid channels 122A can be positioned diametrically opposed to or on opposite sides of the raised inner surface 132 from the pair of inner apertures 128 of the second pair of fluid channels 122B.

FIG. 1C also illustrates that each of the haptics 104 (e.g., any of the first haptic 104A or the second haptic 104B) can have an optic attachment end 136 and a closed free end 138. A haptic fluid port 140 can be defined at the optic attachment end 136 of the haptic 104. The haptic fluid port 140 can serve as a chamber opening of the haptic fluid chamber 120. Fluid within the haptic fluid chamber 120 can flow out of the haptic fluid chamber 120 through the haptic fluid port 140 and into the optic fluid chamber 110 via the pair of fluid channels 122 when the haptic 104 is coupled to the optic portion 102. Similarly, fluid within the optic fluid chamber 110 can flow out of the optic fluid chamber 110 through the pair of fluid channels 122 and into the haptic fluid chamber 120 through the haptic fluid port 140.

As shown in FIGS. 1A and 1C, a haptic 104 can couple to the optic portion 102 at a reinforced portion 126. For example, the first haptic 104A can couple or be attached to the optic portion 102 at the first reinforced portion 126A and the second haptic 104B can couple or be attached to the optic portion 102 at the second reinforced portion 126B.

More specifically, the haptic attachment end 136 can couple to the protruding outer surface 134 of the posterior element 108. The protruding outer surface 134 can also be referred to as a "landing" or "haptic attachment landing." The protruding outer surface 134 can extend out radially from an outer peripheral surface 142 of the optic portion 102. For example, the protruding outer surface 134 can extend out radially from an outer peripheral surface 142 of the posterior element 108 of the optic portion 102. The protruding outer surface 134 can extend out radially from the outer peripheral surface 142 between about 10 microns and 1.0 mm or between about 10 microns and 500 microns.

The haptic attachment end 136 can have a substantially flat surface to adhere or otherwise couple to a substantially flat surface of the protruding outer surface 134. When the haptic attachment end 136 is coupled to the protruding outer surface 134, the haptic fluid port 140 can surround the outer apertures 130 of the fluid channels 122. The haptics 104 can be coupled or adhered to the optic portion 102 via biocompatible adhesives. In some embodiments, the adhesives can be the same adhesives used to couple or adhere the anterior element 106 to the posterior element 108.

Each of the haptics 104 can also comprise a radially outer portion 144 configured to face and contact an inner surface of a patient's capsular bag when the toric AIOL 100 is implanted within the capsular bag. Each of the haptics 104 can also comprise a radially inner portion 146 configured to face the outer peripheral surface 142 of the optic portion 102. Engagement of the capsular bag with the radially outer portion 144 of the haptics 104 will be discussed in more detail in the following sections.

The optic portion 102 can have a base power or base spherical power. The base power of the optic portion 102 can be configured to change based on an internal fluid pressure within the fluid-filled optic fluid chamber 110. The base power of the optic portion 102 can be configured to increase or decrease as fluid enters or exits the optic fluid chamber 110.

The base power of the optic portion 102 can be configured to increase as fluid enters the optic fluid chamber 110 from the haptic fluid chamber(s) 120. The base power of the optic portion 102 can be configured to decrease as fluid exits or is drawn out of the optic fluid chamber 110 into the haptic fluid chamber(s) 120.

The optic portion 102 can be made in part of a deformable or flexible material. In some embodiments, the optic portion 102 can be made in part of a deformable or flexible polymeric material. For example, the anterior element 106, the posterior element 108, or a combination thereof can be made in part of a deformable or flexible polymeric material. The one or more haptics 104 (e.g., the first haptic 104A, the second haptic 104B, or a combination thereof) can be made in part of the same deformable or flexible material as the optic portion 102. In other embodiments, the one or more haptics 104 can be made in part of different materials from the optic portion 102.

In some embodiments, the optic portion 102 can be made in part of a cross-linked copolymer comprising a copolymer blend. The copolymer blend can comprise an alkyl acrylate or methacrylate, a fluoro-alkyl (meth)acrylate, and a phenyl-alkyl acrylate. It is contemplated by this disclosure and it should be understood by one of ordinary skill in the art that these types of acrylic cross-linked copolymers can be generally copolymers of a plurality of acrylates, methacrylates, or a combination thereof and the term "acrylate" as used herein can be understood to mean acrylates, methacrylates, or a combination thereof interchangeably unless otherwise specified. The cross-linked copolymer used to make the optic portion 102 can comprise or be made in part of an alkyl acrylate in the amount of about 3% to 20% (wt %), a fluoro-alkyl acrylate in the amount of about 10% to 35% (wt %), and a phenyl acrylate in the amount of about 50% to 80% (wt %). More specifically, in some embodiments, the cross-linked copolymer can comprise or be made in part of an n-butyl acrylate in the amount of about 3% to 20% (wt %) (e.g., between about 12% to 16%), a trifluoroethyl methacrylate in the amount of about 10% to 35% (wt %) (e.g., between about 17% to 21%), and a phenylethyl acrylate in the amount of about 50% to 80% (wt %) (e.g., between about 64% to 67%). The final composition of the cross-linked copolymer used to make the optic portion 102 can also comprise a cross-linker or cross-linking agent such as ethylene glycol dimethacrylate (EGDMA). For example, the final composition of the cross-linked copolymer can comprise a cross-linker or cross-linking agent (e.g., EGDMA) in the amount of about 1.0%. The final composition of the cross-linked copolymer used to make the optic portion 102 can also comprise an initiator or initiating agent (e.g., Perkadox 16) and a UV absorber.

The haptic(s) 104 can also comprise or be made in part of a cross-linked copolymer comprising a copolymer blend. The copolymer blend can comprise an alkyl acrylate, a fluoro-alkyl acrylate, and a phenyl acrylate. For example, the cross-linked copolymer used to make the haptic(s) 104 can comprise or be made in part of an alkyl acrylate in the amount of about 10% to 25% (wt %), a fluoro-alkyl acrylate in the amount of about 10% to 35% (wt %), and a phenyl acrylate in the amount of about 50% to 80% (wt %). More specifically, in some embodiments, the cross-linked copolymer can comprise or be made in part of an n-butyl acrylate in the amount of about 10% to 25% (wt %) (e.g., between about 19% to about 23%), a trifluoroethyl methacrylate in the amount of about 10% to 35% (wt %) (e.g., between about 14% to about 18%), and a phenylethyl acrylate in the amount of about 50% to 80% (wt %) (e.g., between about 58% to about 62%). The final composition of the cross-linked copolymer used to make the haptic(s) 104 can also comprise a cross-linker or cross-linking agent such as EGDMA. For example, the haptic(s) 104 can comprise a cross-linker or cross-linking agent (e.g., EGDMA) in the amount of about 1.0%. The haptic(s) 104 can also comprise a number of photoinitiators or photoinitiating agents.

In some embodiments, the refractive index of the polymeric materials or composite materials used to make the optic portion 102 can be between about 1.48 and about 1.53. In certain embodiments, the refractive index of the polymeric materials or composite materials used to make the optic portion 102 can be between about 1.50 and about 1.53 (or about 1.5178).

The optic portion 102 can be configured to deform, flex, or otherwise change shape in response to fluid entering or exiting the optic fluid chamber 110. The optic portion 102 can be configured to deform, flex, or otherwise change shape as a result of the material composition (e.g., the polymeric composition) of the optic portion 102 discussed heretofore. The haptic(s) 104 can also be configured to deform or otherwise change shape in response to interactions or engagement with the capsular bag of a patient when the toric AIOL 100 is implanted within an eye of the patient. The haptic(s) 104 can be configured to deform or otherwise change shape as a result of the material composition (e.g., the polymeric composition) of the haptics 104 discussed heretofore.

In some embodiments, the anterior element 106 can be configured to deform, flex, or otherwise change shape (e.g., change its curvature) in response to the fluid entering or exiting the optic fluid chamber 110. In other embodiments, the posterior element 108 can be configured to deform, flex, or otherwise change shape (e.g., change its curvature) in response to the fluid entering or exiting the optic fluid chamber 110. In further embodiments, both the anterior element 106 and the posterior element 108 can be configured to deform, flex, or otherwise change their shapes in response to the fluid entering or exiting the optic fluid chamber 110.

In some embodiments, the fluid within the optic fluid chamber 110, the haptic fluid chamber(s) 120, or a combination thereof can be an oil. More specifically, in certain embodiments, the fluid within the optic fluid chamber 110, the haptic fluid chamber(s) 120, or a combination thereof can be a silicone oil or fluid. Fluid can flow between the optic fluid chamber 110 and the haptic fluid chamber(s) 120 in response to a deformation, flexing, or shape change undertaken by the haptic(s) 104, component(s) of the optic portion 102 (e.g., the anterior element 106, the posterior element 108, or a combination thereof), or a combination thereof.

The fluid within the optic fluid chamber 110, the haptic fluid chamber(s) 120, or a combination thereof can be a silicone oil or fluid comprising or made in part of a diphenyl siloxane. In other embodiments, the silicone oil or fluid can comprise or be made in part of a ratio of two dimethyl siloxane units to one diphenyl siloxane unit. More specifically, in some embodiments, the silicone oil or fluid can be a diphenyltetramethyl cyclotrisiloxane. In additional embodiments, the silicone oil or fluid can comprise or be made in part of a diphenyl siloxane and dimethyl siloxane copolymer.

The fluid (e.g., the silicone oil) can be index matched with the polymeric materials or composites used to make the optic portion 102. When the fluid is index matched with the polymeric materials or composites used to make the optic portion 102, the entire optic portion 102 containing the fluid acts as a single lens. For example, the fluid can be selected so that it has a refractive index of between about 1.48 and 1.53 (or between about 1.50 and 1.53, such as about 1.5178). In some embodiments, the fluid (e.g., the silicone oil) can have a polydispersity index of between about 1.2 and 1.3. In other embodiments, the fluid (e.g., the silicone oil) can have a polydispersity index of between about 1.3 and 1.5. In other embodiments, the fluid (e.g., the silicone oil) can have a polydispersity index of between about 1.1 and 1.2. Other example fluids are described in U.S. Patent Publication No. 2018/0153682, which is herein incorporated by reference in its entirety.

The base power of the optic portion 102 can be configured to change in response to the shape change undertaken by the shape-changing components of the optic portion 102 (e.g., the anterior element 106, the posterior element 108, or a combination thereof). The optic portion 102 can be configured to change shape in response to a physiologic muscle movement (e.g., ciliary muscle movement) undertaken by a patient when the toric AIOL 100 is implanted within a capsular bag of the eye of the patient and the toric AIOL 100 deforms or changes shape in response to ciliary muscle related capsular bag reshaping.

The toric AIOL 100 can be implanted or introduced into a patient's capsular bag after a native lens has been removed from the capsular bag. The patient's capsular bag is connected to zonule fibers which are connected to the patient's ciliary muscles. The capsular bag is elastic and ciliary muscle movements can reshape the capsular bag via the zonule fibers. For example, when the ciliary muscles relax, the zonules are stretched. This stretching pulls the capsular bag in the generally radially outward direction due to radially outward forces. This pulling of the capsular bag causes the capsular bag to elongate, creating room within the capsular bag. When the patient's native lens is present in the capsular bag, the native lens normally becomes flatter (in the anterior-to-posterior direction), which reduces the power of the lens, allowing for distance vision. In this configuration, the patient's native lens is said to be in a disaccommodated state or undergoing disaccommodation.

When the ciliary muscles contract, however, as occurs when the eye is attempting to focus on near objects, the radially inner portion of the muscles move radially inward, causing the zonules to slacken. The slack in the zonules allows the elastic capsular bag to contract and exert radially inward forces on a lens within the capsular bag. When the patient's native lens is present in the capsular bag, the native lens normally becomes more curved (e.g., the anterior part of the lens becomes more curved), which gives the lens more power, allowing the eye to focus on near objects. In this configuration, the patient's native lens is said to be in an accommodated state or undergoing accommodation.

Therefore, any AIOLs implanted within the capsular bag should also possess mechanisms which allow for the base power of the AIOL to increase when the ciliary muscles contract and allow for the base power of the AIOL to decrease when the ciliary muscles relax.

In the present case, when the toric AIOL 100 is implanted or otherwise introduced into a patient's native capsular bag, the radially outer portions 144 of the haptics 104 of the toric AIOL 100 can directly engage with or be in physical contact with the portion of the capsular bag that is connected to the zonules or zonule fibers. Therefore, the radially outer portions 144 of the haptics 104 can be configured to respond to capsular bag reshaping forces that are applied radially when the zonules relax and stretch as a result of ciliary muscle movements.

When the ciliary muscles contract, the peripheral region of the elastic capsular bag reshapes and applies radially inward forces on the radially outer portions 144 of the haptics 104 (for example, the elastic capsular bag applies radially inward forces on the radially outer portion 144 of the first haptic 104A and on the radially outer portion 144 of the second haptic 104B). The radially outer portions 144 of the haptics 104 then deform or otherwise changes shape and this deformation or shape change causes the volume of the haptic fluid chambers 120 to decrease. When the volume of the haptic fluid chambers 120 decreases, the fluid within the haptic fluid chambers 120 is moved or pushed into the optic fluid chamber 110 within the optic portion 102. As discussed previously, fluid moves from the haptic fluid chamber 120 into the optic fluid chamber 110 through fluid channels 122 (e.g., a pair of fluid channels 122) formed within the optic portion 102.

The optic portion 102 (any of the anterior element 106, the posterior element 108, or a combination thereof) can change shape (increase its curvature) in response to the fluid entering the optic fluid chamber 110 from the haptic fluid chambers 120. This increases the base power or base spherical power of the toric AIOL 100 and allows a patient with the toric AIOL 100 implanted within the eye of the patient to focus on near objects. The toric AIOL 100 can also be considered to be in an accommodated state or have undergone accommodation.

When the ciliary muscles relax, the peripheral region of the elastic capsular bag is stretched radially outward and the capsular bag elongates and more room is created within the capsular bag. The radially outer portions 144 of the haptics 104 can be configured to respond to this capsular bag reshaping by returning to its non-deformed or non-stressed configuration. This causes the volume of the haptic fluid chambers 120 to increase or return to its non-deformed volume. This increase in the volume of the haptic fluid chambers 120 causes the fluid within the optic fluid chamber 110 to be drawn out or otherwise flow out of the optic fluid chamber 110 and back into the haptic fluid chambers 120. As discussed previously, fluid moves out of the optic fluid chamber 110 into the haptic fluid chamber 120 through the same fluid channels 122 (e.g., a pair of fluid channels 122) formed within the optic portion 102.

As previously discussed, the optic portion 102 (any of the anterior element 106, the posterior element 108, or a combination thereof) can change shape (decrease its curvature or become flatter) in response to the fluid exiting the optic fluid chamber 110 and into the haptic fluid chambers 120. This decreases the base power or base spherical power of the toric AIOL 100 and allows a patient with the toric AIOL 100 implanted within the eye of the patient to focus on distant objects or provide for distance vision. The toric AIOL 100 can also be considered to be in a disaccommodated state or have undergone disaccommodation.

As shown in FIGS. 1B and 1C, the radially inner portion 146 of the haptics 104 can be designed to be thicker or bulkier (relative to the radially outer portion 144) to provide the haptics 104 with stiffness or resiliency in the anterior-to-posterior direction. This way, when capsular bag forces are applied to the haptics 104 in the anterior-to-posterior direction, less deformation occurs and less fluid movement occurs between the haptic fluid chambers 120 and the optic fluid chamber 110 than when forces are applied in the radial direction. Since less fluid movement occurs, less changes in the base power of the toric AIOL 100 occur when forces are applied to the toric AIOL 100 in the anterior-to-posterior direction. Thus, the design and material properties of the haptics 104 and the optic portion 102 can allow the toric AIOL 100 to maintain a high degree of sensitivity to radial forces applied to the haptics 104 by capsular bag reshaping caused by ciliary muscle movements.

In some embodiments, the anterior element 106 can be configured such that the anterior optical surface 112 changes shape from a spherical surface configuration to an aspherical surface configuration in response to fluid entering the optic fluid chamber 110. An aspherical surface configuration can correct for high order aberrations such as spherical aberration. The fluid can enter the optic fluid chamber 110 from one or more haptic fluid chambers 120 coupled to the optic portion 102 in response to ciliary muscle movement.

The anterior optical surface 112 can be stressed into the aspherical surface configuration as a center or central portion of the anterior element 106 flexes or bulges out further than an outer periphery of the anterior element 106 which is held down by adhesive or an adhesive layer 148 (see FIG. 1B).

In other embodiments, the posterior element 108 can be configured such that the posterior optical surface 116 changes shape from a spherical surface configuration to an aspherical surface configuration in response to fluid entering the optic fluid chamber 110.

The posterior optical surface 116 can be stressed into the aspherical surface configuration as a center or central portion of the posterior element 108 flexes or bulges out further than an outer periphery of the anterior element 106 which is held down by adhesive or the adhesive layer 148.

The anterior element 106 can be attached or otherwise adhered to the posterior element 108 via the adhesive layer 148. The adhesive layer 148 can be substantially annular-shaped. The adhesive layer 148 can be positioned at a peripheral edge 150 (see FIG. 1C) of the optic portion 102 in between the anterior element 106 and the posterior element 108. For example, the adhesive layer 148 can be positioned on top of the raised inner surface 132 of the posterior element 108.

The adhesive layer 148 or adhesive can comprise or be made in part of a biocompatible adhesive. The adhesive layer 148 or adhesive can comprise or be made in part of a biocompatible polymeric adhesive.

The adhesive layer 148 or adhesive can comprise or be made in part of a cross-linkable polymer precursor formulation. The cross-linkable polymer precursor formulation can comprise or be made in part of a copolymer blend, a hydroxyl-functional acrylic monomer, and a photoinitiator (e.g., Darocur 4265 or a 50/50 blend of diphenyl(2,4,6-trimethylbenzoyl)phosphine oxide and 2-hydroxy2-methyl-propiophenone). The copolymer blend can comprise an alkyl acrylate (e.g., n-butyl acrylate in the amount of about 41% to about 45% (wt %)), a fluoro-alkyl acrylate (e.g., trifluoroethyl methacrylate in the amount of about 20% to about 24% (wt %)), and a phenyl-alkyl acrylate (phenylethyl acrylate in the amount of about 28% to about 32% (wt %)). The hydroxyl-functional acrylic monomer can be 2-hydroxyethyl acrylate (HEA) in the amount of about 0.5 to 5.0 wt %, preferably about 1.0% to about 2.0 wt %. The photoinitiator can be used to facilitate curing of the hydroxyl-functional pre-polymer.

The first step in making the adhesive is preparation of a hydroxyl-functional polymer precursor by photopolymerizing the cross-linkable polymer precursor formulation, thereby yielding a cured composition. The second step is chemical conversion of the precursor polymer pendant hydroxyl moieties, or hydroxyl pendant groups, into pendant methacrylate functional groups by reacting with a methacrylic anhydride or methacryloyl chloride, thus forming a methacrylic-functional cross-linkable polymer comprising the alkyl acrylate or methacrylate (e.g., n-butyl acrylate), the fluoro-alkyl (meth)acrylate (e.g., trifluoroethyl methacrylate), the phenyl-alkyl acrylate (phenylethyl acrylate), and 2-(2-methyl-acryloyloxy)ethyl acrylate.

The methacrylic-functional cross-linkable polymer can be blended with a reactive acrylic monomer diluent such as 1-adamantyl methacrylate (ADMA) and the same photoinitiator (e.g., Darocur 4265). For example, the final composition of the adhesive can comprise the methacrylic-functional cross-linkable polymer in the amount of about 50% to about 85% (wt %) (e.g., about 61% to about 65%), the reactive acrylic monomer diluent in the amount of about 10% to about 40% (wt %) (32% to about 36%), and the photoinitiator (e.g., Darocur 4265) in the amount of about 2% to about 3% (wt %).

The adhesive or adhesive layer 148 can bond or otherwise join the anterior element 106 to the posterior element 108. The adhesive can also bond or join the haptic(s) 104 to the optic portion 102.

In some embodiments, the anterior optical surface 112 of the anterior element 106 can be manufactured to have an aspherical optical surface prior to the toric AIOL 100 being implanted within the eye of the patient. In these embodiments, the anterior optical surface 112 can be aspheric regardless of any fluid pressure changes within the optic fluid chamber 110. In these embodiments, the anterior optical surface 112 can also maintain its asphericity across all base power changes.

In other embodiments, the posterior optical surface 116 of the posterior element 108 can be manufactured to have an aspherical optical surface prior to the toric AIOL 100 being implanted within the eye of the patient. In these embodiments, the posterior optical surface 116 can be aspheric regardless of any fluid pressure changes within the optic fluid chamber 110. In these embodiments, the posterior optical surface 116 can maintain its asphericity across all base power changes.

In some embodiments, the anterior element 106 can have a thickness at its center or central portion that is greater than a thickness at its periphery. In certain embodiments, the posterior element 108 can also have a thickness at its center or central portion that is greater than a thickness at its periphery.

As shown in FIGS. 1B and 1C, the optic portion 102 can have an optical axis 152. The optical axis 152 can extend in an anterior-to-posterior direction through a center or center point of the optic portion 102. The optical axis 152 can extend through the centers or center points of both the anterior element 106 and the posterior element 106.

The thickness of the anterior element 106 can be greater at the optical axis 152 or near the optical axis 152 than at the periphery of the anterior element 106. In some embodiments, the thickness of the anterior element 106 can increase gradually from the periphery of the anterior element 106 toward the optical axis 152.

In certain embodiments, the thickness of the anterior element 106 at the optical axis 152 or near the optical axis 152 can be between about 0.200 mm and about 0.300 mm (or about 0.280 mm). In these and other embodiments, the thickness of the anterior element 106 near the periphery can be between about 0.100 mm and about 0.200 mm (or about 0.135 mm). This difference in thickness can contribute to the anterior optical surface 112 changing shape from the spherical surface configuration to the aspherical surface configuration as fluid enters the fluid-filled optic fluid chamber 110 from the haptic fluid chamber(s) 120.

Moreover, the anterior inner surface 114 of the anterior element 106 can have less curvature or be flatter than the anterior optical surface 112. This difference in surface curvature between the anterior inner surface 114 and the anterior optical surface 112 can also contribute to the anterior optical surface 112 changing shape from the spherical surface configuration to the aspherical surface configuration as fluid enters the fluid-filled optic fluid chamber 110 from the haptic fluid chamber(s) 120.

In other embodiments, the thickness of the posterior element 108 can be greater at the optical axis 152 or near the optical axis 152 than portions of the posterior element 108 radially outward from the optical axis 152 but prior to reaching the raised inner surface 132. The thickness of the posterior element 108 can gradually decrease from the optical axis 152 to portions radially outward from the optical axis 152 (but prior to reaching the raised inner surface 132). The thickness of the posterior element 108 can increase again from the beginning of the raised inner surface 132 to peripheral edge 150.

In certain embodiments, the thickness of the posterior element 108 at the optical axis 152 or near the optical axis 152 can be between about 0.40 mm and about 0.50 mm (or about 0.43 mm). In these and other embodiments, the thickness of the posterior element 108 radially outward from the optical axis 152 (but prior to reaching the raised inner surface 132) can be between about 0.30 mm and about 0.40 mm (or about 0.38 mm). The thickness of the posterior element 108 near the peripheral edge 150 can be between about 1.00 mm and 1.20 mm (or about 1.188 mm). This difference in thickness can contribute to the posterior optical surface 116 changing shape from the spherical surface configuration to the aspherical surface configuration as fluid enters the fluid-filled optic fluid chamber 110 from the haptic fluid chamber(s) 120.

Moreover, the posterior inner surface 118 of the posterior element 108 can have less curvature or be flatter than the posterior optical surface 116. This difference in surface curvature between the posterior inner surface 118 and the posterior optical surface 116 can also contribute to the posterior optical surface 116 changing shape from the spherical surface configuration to the aspherical surface configuration as fluid enters the fluid-filled optic fluid chamber 110 from the haptic fluid chamber(s) 120.

One technical problem faced by the applicants is how to introduce both toricity and asphericity to an accommodating intraocular lens. An accommodating intraocular lens that can correct for both corneal astigmatism and spherical aberration can allow cataract patients suffering from such higher order aberrations to rely on only one pair of accommodating intraocular lenses to correct for such aberrations rather than still having to rely on corrective eyewear.

One solution discovered by the applicants is to separate the optical surface configured to change into the aspherical surface configuration from the external optical surface having the toric lens surface or cylinder. For example, the toric AIOL 100 can be configured such that the aspheric optical surface is on an opposite lens element from the lens element having the toric optical surface or cylinder.

In some embodiments, the posterior element 108 can be shaped to have a toric lens surface or cylinder profile and the anterior element 106 can be configured such that the anterior optical surface 112 is aspheric or changes shape from a spherical surface configuration to an aspherical surface configuration in response to fluid entering the fluid-filled optic fluid chamber 110 from the haptic fluid chamber(s) 120.

In other embodiments, the anterior element 106 can be shaped to have a toric lens surface or cylinder profile and the posterior element 108 can be configured such that the posterior optical surface 116 is aspheric or changes shape from a spherical surface configuration to an aspherical surface configuration in response to fluid entering the fluid-filled optic fluid chamber 110 from the haptic fluid chamber(s) 120.

As shown in FIG. 1A, the toric AIOL 100 can be oriented by a midline 154. The midline 154 can be a line or axis that substantially bisects the optic portion 102 or divides the optic portion 102 substantially in half. In some embodiments, the midline 154 can substantially bisect the haptic-optic interface 124 or extend through a midportion of the haptic-optic interface 14. For example, the midline 154 can substantially bisect both a first haptic-optic interface and a second haptic-optic interface diametrically opposed to the first haptic-optic interface. The midline 154 can also extend through or substantially bisect the first reinforced portion 126A and the second reinforced portion 126B.

As previously discussed, the optic portion 102 can comprise at least one pair of fluid channels 122 configured to place the fluid-filled optic fluid chamber 110 in fluid communication with a haptic fluid chamber 120. The midline 154 can extend in between the pair of fluid channels 122 or substantially bisect a part of the optic portion 102 separating the pair of fluid channels 122.

In some embodiments, the midline 154 can extend in between a pair of apertures (any of the inner apertures 128 or the outer apertures 130) or bisect a part of the optic portion 102 separating a pair of apertures disposed at the ends of the pair of fluid channels 122. For example, the optic portion 102 can comprise a first pair of fluid channels 122A and a second pair of fluid channels 122B. The midline 154 can extend in between or substantially bisect a portion separating the first pair of fluid channels 122A and the second pair of fluid channels 122B. The midline 154 will be discussed in more detail with respect to an orientation or placement location of certain meridians of the toric AIOL 100.

Figure 2A:
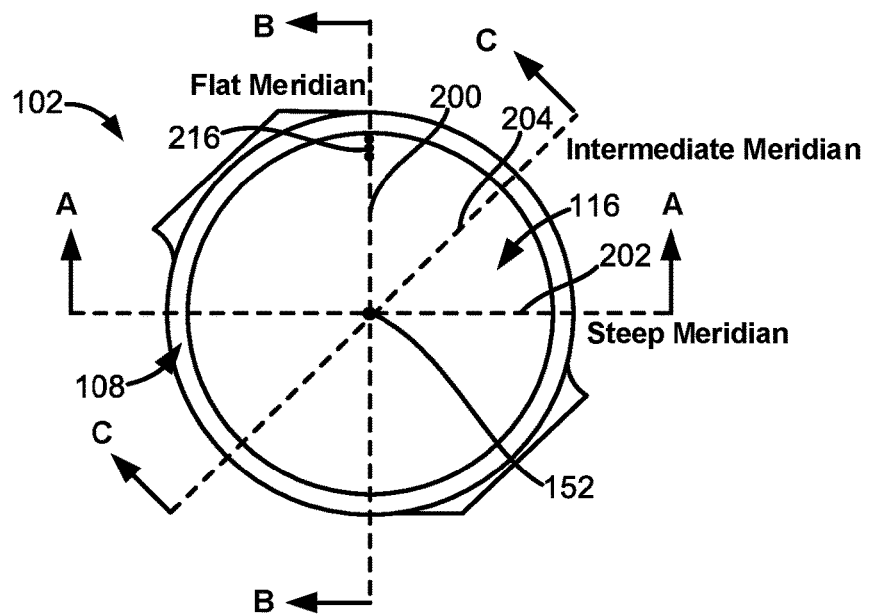
FIG. 2A illustrates a top plan view of a posterior element of an embodiment of the toric accommodating intraocular lens.

FIG. 2A illustrates a top plan view of an embodiment of a posterior element 108 of the toric AIOL 100. The posterior optical surface 116 can be shaped such that a radius of curvature of the posterior optical surface 116 differs along different optical surface meridians. For example, the radius of curvature along a flat meridian 200 of the posterior optical surface 116 differs from the radius of curvature along a steep meridian 202 of the posterior optical surface 116.

In some embodiments, the radius of curvature of the posterior optical surface 116 can vary periodically around the posterior optical surface 116. The radius of curvature of the posterior optical surface 116 can vary periodically around the posterior optical surface 116 when the radius of curvature changes continuously in a periodic manner along different optical surface meridians (for example, when the optical surface meridian is rotated about the optical axis 152 or a centerpoint of the posterior optical surface 116). In certain embodiments, the radius of curvature of the posterior optical surface 116 can vary sinusoidally around the posterior optical surface 116.

As shown in FIG. 2A, the posterior optical surface 116 can comprise a flat meridian 200 and a steep meridian 202 oriented or positioned substantially perpendicular to the flat meridian 200. For example, the flat meridian 200 can be separated from the steep meridian 202 by a rotational angle of about 90 degrees.

Figure 2B:
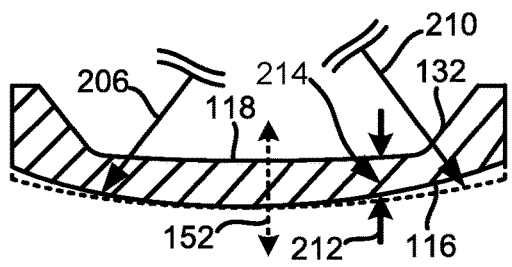
FIG. 2B illustrates a sectional view of the posterior element taken along cross-section A-A of FIG. 2A.
Figure 2C:
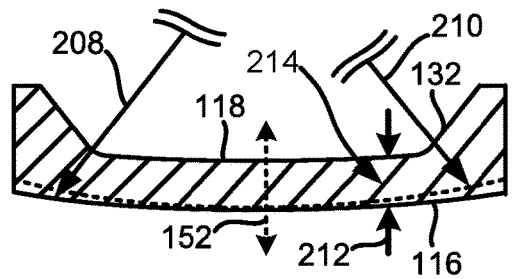
FIG. 2C illustrates a sectional view of the posterior element taken along cross-section B-B of FIG. 2A.

FIG. 2B illustrates a sectional view of the posterior element 108 taken along the steep meridian 202 (as indicated by cross-section A-A of FIG. 2A). FIG. 2C illustrates a sectional view of the posterior element 108 taken along the flat meridian 200 (as indicated by cross-section B-B of FIG. 2A). Moreover, FIG. 2D illustrates a sectional view of the posterior element 108 taken along an intermediate meridian 204 oriented at a rotational angle of about 45 degrees from both the flat meridian 200 and the steep meridian 202 (as indicated by cross-section C-C of FIG. 2A).

A refractive dioptric power of the posterior optical surface 116 can be the greatest along the steep meridian 202 of the posterior optical surface 116. The refractive dioptric power of the posterior optical surface 116 can be the least along the flat meridian 200 of the posterior optical surface 116. The steep meridian 202 and the flat meridian 200 can be considered the principal meridians of the lens. The flat meridian 200 can also be referred to as the cylinder axis or simply "axis" of a toric lens.

Figure 2D:
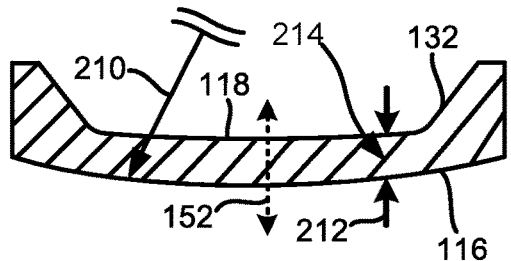
FIG. 2D illustrates a sectional view of the posterior element taken along cross-section C-C of FIG. 2A.

As shown in FIGS. 2B-2D, the posterior optical surface 116 can comprise or be defined by a steep meridian radius-of-curvature (ROC) 206, a flat meridian ROC 208, and an intermediate meridian ROC 210. More specifically, as shown in FIG. 2B, the intermediate meridian ROC 210 can be greater than the steep meridian ROC 206. The surface contour of the posterior optical surface 116 along the intermediate meridian 204 is shown in broken lines in both FIGS. 2B and 2C. In these embodiments, the steep meridian ROC 206 is also less than the flat meridian ROC 208.

As shown in FIG. 2C, the flat meridian ROC 208 can be greater than the intermediate meridian ROC 210. In addition, the flat meridian ROC 208 can also be greater than the steep meridian ROC 206.

As shown in FIGS. 2A-2D, the radius of curvature of the posterior optical surface 116 can vary sinusoidally around the posterior optical surface 116. For example, the radius of curvature of the posterior optical surface 116 can increase gradually (when viewing the radius of curvature along different surface meridians) from the steep meridian 202 to the intermediate meridian 204 and then continue to increase until reaching the flat meridian 200. The radius of curvature of the posterior optical surface 116 can then decrease gradually from the flat meridian 200 to the intermediate meridian 204 and then continue to decrease until reaching the steep meridian 202 again after a 180 degrees rotation. This periodic change in the radius of curvature of the posterior optical surface 116 can continue for the full 360 degrees or until returning once again to the steep meridian 202.

FIGS. 2B-2D also illustrate that a posterior element thickness 212 can vary along different optical surface meridians. The posterior element thickness 212 can be a thickness or height of the posterior element 108 as measured from the posterior inner surface 118 to the posterior optical surface 116.

The posterior element thickness 212 at or near a radially peripheral portion 214 of the posterior element 108 can vary along different optical surface meridians. The radially peripheral portion 214 can be a portion of the posterior element 108 at a peripheral edge of the posterior element 108. In some embodiments, the radially peripheral portion 214 can be a portion of the posterior element 108 in between the optical axis 152 and the raised inner surface 132. More specifically, the radially peripheral portion 214 can be a portion of the posterior element 108 closer to the raised inner surface 132 (in terms of radial distance) than the optical axis 152.

In some embodiments, the posterior element thickness 212 at or near the radially peripheral portion 214 can be the greatest (or thickest) along the flat meridian 200. In these embodiments, the posterior element thickness 212 at or near the radially peripheral portion 214 can be the least (or thinnest) along the steep meridian 202. The posterior element thickness 212 at or near the radially peripheral portion 214 can also vary periodically around the posterior element 108 (for example, when the optical surface meridian is rotated about the optical axis 152 or a centerpoint of the posterior optical surface 116). Moreover, the posterior element thickness 212 at or near the radially peripheral portion 214 can also vary sinusoidally around the posterior element 108.

In certain embodiments, the posterior element thickness 212 at or near the optical axis 152 (or at or near the centerpoint of the posterior optical surface 116) can be the same along different optical surface meridians. For example, the posterior element thickness 212 at or near the optical axis 152 (or at or near the centerpoint of the posterior optical surface 116) can be the same along both the steep meridian 202 and the flat meridian 200.

In some embodiments, the posterior element thickness 212 at or near the radially peripheral portion 214 along the flat meridian 200 can be between about 0.38 mm and about 0.45 mm. In these embodiments, the posterior element thickness 212 at or near the radially peripheral portion 214 along the steep meridian 202 can be between about 0.30 mm and about 0.40 mm.

The posterior element 108 can further comprise a posterior inner surface 118. The posterior inner surface 118 can be a surface of the posterior element 108 facing the optic fluid chamber 110. In some embodiments, at least part of the posterior inner surface 118 can serve as a chamber wall of the optic fluid chamber 110. The posterior inner surface 118 can be rotationally symmetric or substantially rotationally symmetric. The posterior inner surface 118 can be rotationally symmetric when the radius of curvature of the posterior inner surface 118 is the same along all surface meridians. For example, the radius of curvature of the posterior inner surface 118 can be between about 50.0 mm and 70.0 mm (or about 60.0 mm).

The toric AIOL 100 can also be designed or configured to have a set cylinder power. Cylinder power can refer to the dioptric power of the toric AIOL 100 along its steep meridian. The cylinder power is often expressed as a difference in dioptric power (e.g., +1.0 D or +3.0 D) provided by the steep curvature of the toric lens along its steep meridian.

In some embodiments, a toric AIOL 100 having the toric posterior optical surface 116 as described heretofore can have a cylinder power of between about +0.75 D to about +6.00 D. For example, the toric AIOL 100 having the toric posterior optical surface 116 as described heretofore can have a cylinder power of about +0.75 D, +1.50 D, +2.25 D, +3.00 D, +3.75 D, +4.50 D, +5.25 D, or +6.00 D.

Table 1 below presents radius-of-curvature values and posterior element thickness values for two versions of a toric AIOL 100 having a toric posterior optical surface 116 (each with a different cylinder power):

TABLE 1

Low-Cylinder and High-Cylinder Toric AIOL Parameters

| Design | Cylinder Power | Intermediate Meridian ROC (Posterior Optical Surface) | Flat Meridian ROC (Posterior Optical Surface) | Steep Meridian ROC (Posterior Optical Surface) | Peripheral Posterior Element Thickness Along Flat Meridian | Peripheral Posterior Element Thickness Along Steep Meridian |
|---|---|---|---|---|---|---|
| Low-Cylinder | 0.75 D | 36.0 mm | 38.92 mm | 33.49 mm | 0.389 mm | 0.370 mm |
| High-Cylinder | 6.0 D | 36.0 mm | 89.84 mm | 22.51 mm | 0.455 mm | 0.304 mm |

As previously discussed, the base power or base spherical power of the optic portion 102 can be configured to change based on the internal fluid pressure within the fluid-filled optic fluid chamber 110. One technical problem faced by the applicants is how to introduce cylindricity or a toric surface to an accommodating intraocular lens (AIOL) such that the cylinder power of the AIOL remains substantially unchanged or stable across all base power changes throughout accommodation or disaccommodation of the lens.

One solution discovered by the applicants is to vary a radius of curvature of the posterior optical surface 116 while keeping the posterior inner surface 118 (the surface opposite the posterior optical surface 116) rotationally symmetric. As will be discussed in more detail in the following sections, another solution provided by the present disclosure is to orient the flat meridian 200 of the posterior optical surface 116 at an oblique angle to a midline 154 substantially bisecting the optic portion 102.

By designing the toric AIOL 100 in this manner, the cylinder power of the optic portion 102 can be configured to remain substantially unchanged or stable throughout the change in base power of the optic portion 102 in response to changes in the fluid pressure within the fluid-filled optic fluid chamber. For example, the relative refractive dioptric power between the steep meridian 202 and the flat meridian 200 can remain substantially unchanged or stable when the base power of the optic portion 102 changes throughout accommodation and disaccommodation.

FIG. 2A also illustrates that the posterior optical surface 116 can comprise one or more markings 216 disposed on the posterior optical surface 116. The markings 216 can be visually perceptible to a clinician or physician implanting the toric AIOL 100 into the eye of a patient. The one or more markings 216 can be ink markings or dye markings. In other embodiments, the one or more markings 216 can be etchings or surface patterns appearing on the posterior optical surface 116.

In the example embodiments shown in FIG. 2A, the one or markings 216 are shown as small dots or spots. In other embodiments, the one or more markings 216 can be in the form of a line, a dotted line, or other shapes besides circular dots. The one or more markings 216 can help the clinician or physician orient the flat meridian 200 or cylinder axis with respect to markings previously applied to the eye of the patient to mark the patient's corneal astigmatism. For example, the clinician or physician can line up the one or more markings 216 with markings used to indicate the patient's corneal astigmatism to ensure the toric AIOL 100 is properly implanted.

In some embodiments, the anterior optical surface 112 of the toric AIOL 100 can be rotationally symmetric while the posterior optical surface 116 can be toric or have a radius of curvature that differs along different optical surface meridians. In other embodiments, as previously discussed, the anterior optical surface 112 of the toric AIOL 100 can be aspheric while the posterior optical surface 116 can be toric or have a radius of curvature that differs along different optical surface meridians.

FIG. 3A illustrates a top plan view of an embodiment of the anterior element 106 of the toric AIOL 100. In this embodiment, the anterior element 106 can be shaped such that a radius of curvature of the anterior optical surface 112 differs along different optical surface meridians. For example, the radius of curvature along a flat meridian 300 of the anterior optical surface 112 differs from the radius of curvature along a steep meridian 302 of the anterior optical surface 112.

In some embodiments, the radius of curvature of the anterior optical surface 112 can vary periodically around the anterior optical surface 112. The radius of curvature of the anterior optical surface 112 can vary periodically around the anterior optical surface 112 when the radius of curvature changes continuously in a periodic manner along different optical surface meridians (for example, when the optical surface meridian is rotated about the optical axis 152 or a centerpoint of the anterior optical surface 112). In certain embodiments, the radius of curvature of the anterior optical surface 112 can vary sinusoidally around the anterior optical surface 112.

As shown in FIG. 3A, the anterior optical surface 112 can comprise a flat meridian 300 and a steep meridian 302 oriented or positioned substantially perpendicular to the flat meridian 300. For example, the flat meridian 300 can be separated from the steep meridian 302 by a rotational angle of about 90 degrees.

FIG. 3B illustrates a sectional view of the anterior element 106 taken along the steep meridian 302 (as indicated by cross-section A-A of FIG. 3A). FIG. 3C illustrates a sectional view of the same anterior element 106 taken along the flat meridian 300 (as indicated by cross-section B-B of FIG. 3A).

A refractive dioptric power of the anterior optical surface 112 can be the greatest along the steep meridian 302 of the anterior optical surface 112 and the refractive dioptric power of the anterior optical surface 112 can be the least along the flat meridian 300 of the anterior optical surface 112. The steep meridian 302 and the flat meridian 300 can be considered the principal meridians of the lens. The flat meridian 300 can also be referred to as the cylinder axis or simply "axis" of a toric lens.

As shown in FIGS. 3B-3C, the anterior optical surface 112 can comprise or be defined by a steep meridian radius-of-curvature (ROC) 304 and a flat meridian ROC 306. The flat meridian ROC 306 can be greater than the steep meridian ROC 304.

As shown in FIGS. 3A-3C, the radius of curvature of the anterior optical surface 112 can vary sinusoidally around the anterior optical surface 112. For example, the radius of curvature of the anterior optical surface 112 can increase gradually from the steep meridian 302 to an intermediate meridian (i.e., a meridian oriented at a rotational angle of about 45 degrees from both the flat meridian 300 and the steep meridian 302) and then continue to increase until reaching the flat meridian 300. The radius of curvature of the anterior optical surface 112 can then decrease gradually from the flat meridian 300 to the intermediate meridian and then continue to decrease until reaching the steep meridian 302 again after a 180 degrees rotation. This periodic change in the radius of curvature of the anterior optical surface 112 can continue for the full 360 degrees or until returning to the steep meridian 302.

FIGS. 3B and 3C also illustrate that an anterior element thickness 308 can vary along different optical surface meridians. The anterior element thickness 308 can be a thickness or height of the anterior element 106 as measured from the anterior inner surface 114 to the anterior optical surface 112.

The anterior element thickness 308 at or near a radially peripheral portion 310 of the anterior element 106 can vary along different optical surface meridians. The radially peripheral portion 310 can be a portion of the anterior element 106 at a peripheral edge of the anterior element 106. In some embodiments, the radially peripheral portion 310 can be a portion of the anterior element 106 in between the optical axis 152 and the adhesive layer 148. More specifically, the radially peripheral portion 310 can be a portion of the anterior element 106 closer to the adhesive layer 148 (in terms of radial distance) than the optical axis 152.

In some embodiments, the anterior element thickness 308 at or near the radially peripheral portion 310 can be the greatest (or thickest) along the flat meridian 300. In these embodiments, the anterior element thickness 308 at or near the radially peripheral portion 310 can be the least (or thinnest) along the steep meridian 302. The anterior element thickness 308 at or near the radially peripheral portion 310 can also vary periodically around the anterior element 106 (for example, when the optical surface meridian is rotated about the optical axis 152 or a centerpoint of the anterior optical surface 112). For example, the anterior element thickness 308 can vary sinusoidally around the anterior element 106.

In certain embodiments, the anterior element thickness 308 at or near the optical axis 152 (or at or near the centerpoint of the anterior optical surface 112) can be the same along different optical surface meridians. For example, the anterior element thickness 308 at or near the optical axis 152 (or at or near the centerpoint of the anterior optical surface 112) can be the same along both the steep meridian 302 and the flat meridian 300. In one embodiment, the anterior element thickness 308 at or near the optical axis 152 can be about 0.40 mm.

In some embodiments, the anterior element thickness 308 at or near the radially peripheral portion 310 along the flat meridian 300 can be between about 0.140 mm and about 0.210 mm. In these embodiments, the anterior element thickness 308 at or near the radially peripheral portion 310 along the steep meridian 302 can be between about 0.050 mm and about 0.125 mm.

The anterior element 106 can further comprise an anterior inner surface 114. The anterior inner surface 114 can be a surface of the anterior element 106 facing the optic fluid chamber 110. In some embodiments, at least part of the anterior inner surface 114 can serve as a chamber wall of the optic fluid chamber 110. The anterior inner surface 114 can be rotationally symmetric or substantially rotationally symmetric. The anterior inner surface 114 can be rotationally symmetric when the radius of curvature of the anterior inner surface 114 is the same along all surface meridians. For example, the radius of curvature of the anterior inner surface 114 can be between about 50.0 mm and 70.0 mm (or about 60.0 mm).

The toric AIOL 100 can also be designed or configured to have a set cylinder power. Cylinder power can refer to the dioptric power of the toric AIOL 100 along the steep meridian 302. The cylinder power is often expressed as a difference in dioptric power (e.g., +1.0 D or +3.0 D) provided by the steep curvature of the toric lens along its steep meridian.

In some embodiments, a toric AIOL 100 having the toric anterior optical surface 112 as described heretofore can have a cylinder power of between about +0.75 D to about +6.00 D. For example, the toric AIOL 100 having the toric anterior optical surface 112 as described heretofore can have a cylinder power of about +0.75 D, +1.50 D, +2.25 D, +3.00 D, +3.75 D, +4.50 D, +5.25 D, or +6.00 D.

Table 2 below presents radius-of-curvature values and anterior element thickness values for two versions of a toric AIOL 100 having a toric anterior optical surface 112 (each with a different cylinder power):

TABLE 2

Low-Cylinder and High-Cylinder Toric AIOL Parameters

| Design | Cylinder Power | Flat Meridian ROC (Anterior Optical Surface) | Steep Meridian ROC (Anterior Optical Surface) | Peripheral Anterior Element Thickness Along Flat Meridian | Peripheral Anterior Element Thickness Along Steep Meridian |
|---|---|---|---|---|---|
| Low-Cylinder | 0.75 D | 21.28 mm | 19.55 mm | 0.143 mm | 0.123 mm |
| High-Cylinder | 6.0 D | 30.86 mm | 15.21 mm | 0.209 mm | 0.056 mm |

As previously discussed, the base power or base spherical power of the optic portion 102 can be configured to change based on the internal fluid pressure within the fluid-filled optic fluid chamber 110. One technical problem faced by the applicants is how to introduce cylindricity or a toric surface to an accommodating intraocular lens (AIOL) such that the cylinder power of the AIOL remains substantially unchanged or stable across all base power changes throughout accommodation or disaccommodation of the lens.

One solution discovered by the applicants is to vary a radius of curvature of the anterior optical surface 112 while keeping the anterior inner surface 114 (the surface opposite the anterior optical surface 112) rotationally symmetric. As will be discussed in more detail in the following sections, another solution provided by the present disclosure is to orient the flat meridian 300 of the anterior optical surface 112 at an oblique angle to a midline 154 substantially bisecting the optic portion 102.

By designing the toric AIOL 100 in this manner, the cylinder power of the optic portion 102 can be configured to remain substantially unchanged or stable throughout the change in base power of the optic portion 102 in response to changes in the fluid pressure within the fluid-filled optic fluid chamber. For example, the relative refractive dioptric power between the steep meridian 302 and the flat meridian 300 can remain substantially unchanged or stable when the base power of the optic portion 102 changes throughout accommodation and disaccommodation.

FIG. 3A also illustrates that the anterior optical surface 112 can comprise one or more markings 312 disposed on the anterior optical surface 112. The markings 312 can be visually perceptible to a clinician or physician implanting the toric AIOL 100 into the eye of a patient. The one or more markings 312 can be ink markings or dye markings. In other embodiments, the one or more markings 312 can be etchings or surface patterns appearing on the anterior optical surface 112.

In the example embodiments shown in FIG. 3A, the one or markings 312 are shown as small dots or spots. In other embodiments, the one or more markings 312 can be in the form of a line, a dotted line, or other shapes besides circular dots. The one or more markings 312 can help the clinician or physician orient the flat meridian 300 or cylinder axis with respect to markings previously applied to the eye of the patient to mark the patient's corneal astigmatism. For example, the clinician or physician can line up the one or more markings 312 with markings used to indicate the patient's corneal astigmatism to ensure the toric AIOL 100 is properly implanted.

In some embodiments, the posterior optical surface 116 of the toric AIOL 100 can be rotationally symmetric while the anterior optical surface 112 can be toric or have a radius of curvature that differs along different optical surface meridians. In other embodiments, as previously discussed, the posterior optical surface 116 of the toric AIOL 100 can be aspheric while the anterior optical surface 112 can be toric or have a radius of curvature that differs along different optical surface meridians.

Figure 4:
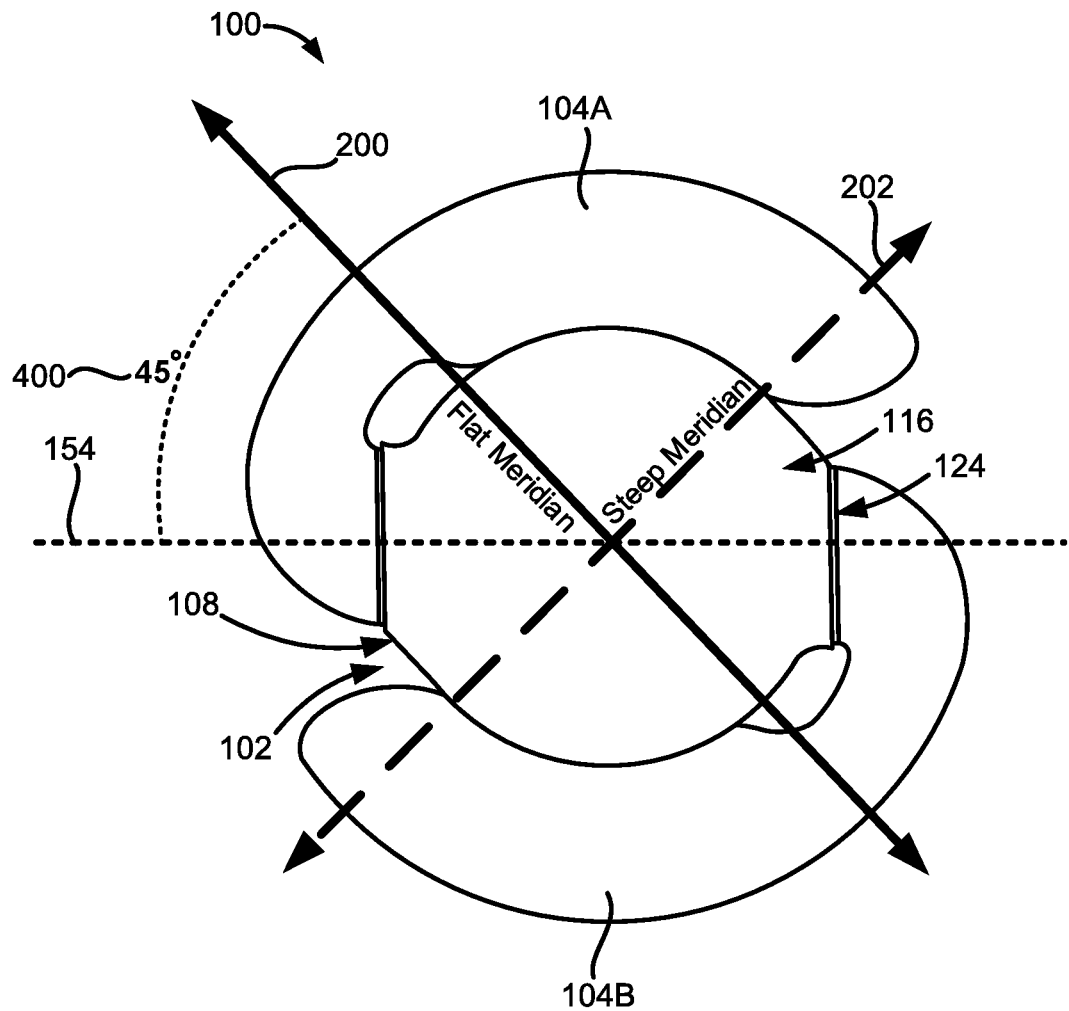
FIG. 4 illustrates an orientation of a flat meridian relative to a midline of the toric accommodating intraocular lens.

FIG. 4 illustrates a cylinder orientation of a flat meridian relative to a midline 154 of the toric AIOL 100. Cylinder orientation can refer to an orientation or positioning of meridians of the lens relative to other feature(s) of the toric AIOL 100 (such as the midline 154). For example, cylinder orientation can refer to the orientation or positioning of a flat meridian (or the "cylinder axis"), a steep meridian, or a combination thereof relative to the eye. Cylinder orientation can also refer to the orientation or positioning of one meridian relative to another meridian.

Although FIG. 4 is shown with respect to the posterior element 108 and the posterior optical surface 116 (including the flat meridian 200 and the steep meridian 202), it is contemplated by this disclosure, and it should be understood by one of ordinary skill in the art, that the flat meridian 300 and steep meridian 302 of the anterior optical surface 112 can also be oriented at an oblique angle 400 to the midline 154.

One technical problem faced by the applicants is how to keep the cylinder orientation of a toric AIOL substantially unchanged or fixed across all base power changes, that is, throughout accommodation or disaccommodation. An unstable cylinder orientation is at best without benefit (that is, has no astigmatic correcting effects) and, at worst, can adversely affect a patient's vision (e.g., induce astigmatism in another meridian).

One solution discovered by the applicants is to orient a flat meridian (for example, any of the flat meridian 200 or the flat meridian 300) at an oblique angle 400 to the midline 154. As previously discussed, in some embodiments, the midline 154 can substantially bisect the optic portion 102. For example, the midline 154 can be a line or axis that substantially bisects the optic portion 102 or divides the optic portion 102 in half.

In other embodiments, the midline 154 can substantially bisect the haptic-optic interface 124 or extend through a midportion of the haptic-optic interface 124. For example, the midline 154 can substantially bisect both a first haptic-optic interface and a second haptic-optic interface (when the toric AIOL 100 has two haptics 104).

The midline 154 can also extend through or substantially bisect a reinforced portion 126. For example, the midline 154 can extend through or substantially bisect the first reinforced portion 126A and the second reinforced portion 126B.

As previously discussed, the optic portion can comprise at least one pair of fluid channels 122 configured to place the fluid-filled optic fluid chamber 110 in fluid communication with a haptic fluid chamber 120. The midline 154 can extend in between the pair of fluid channels 122 or substantially bisect a part of the optic portion 102 separating the pair of fluid channels 122. In some embodiments, the midline 154 can extend in between the pair of apertures (e.g., the inner apertures 128) or bisect a part of the optic portion 102 separating the pair of apertures (e.g., the inner apertures 128) disposed at the end of the pair of fluid channels 122. For example, the optic portion 102 can comprise a first pair of fluid channels 122A and a second pair of fluid channels 122B, the midline 154 can extend in between or substantially bisect a part of the optic portion 102 separating the first pair of fluid channels 122A and the second pair of fluid channels 122B.

The flat meridian (any of the flat meridian 200 or the flat meridian 300) can be oriented or otherwise positioned at an oblique angle 400 to the midline 154. In some embodiments, the oblique angle 400 can be a clockwise rotational angle. For example, the oblique angle 400 can be a clockwise rotational angle of between about 30 degrees and 60 degrees. In certain embodiments, the oblique angle can be a clockwise rotational angle of about 45 degrees. As previously discussed, the flat meridian 200 can be substantially perpendicular to or oriented 90 degrees from the steep meridian 202.

By designing the toric AIOL 100 in this manner, the cylinder orientation of the optic portion 102 can remain substantially unchanged throughout the change in base power of the optic portion 102 resulting from changes in the internal fluid pressure within the fluid-filled optic fluid chamber 110. For example, the orientation or positioning of the flat meridian and the steep meridian of the toric AIOL 100 can remain substantially unchanged or fixed relative to the corneal astigmatism axis of a patient's eye once the toric AIOL 100 is implanted within the patient's eye (even when the base power of the optic portion changes throughout accommodation and disaccommodation).

Figure 5:
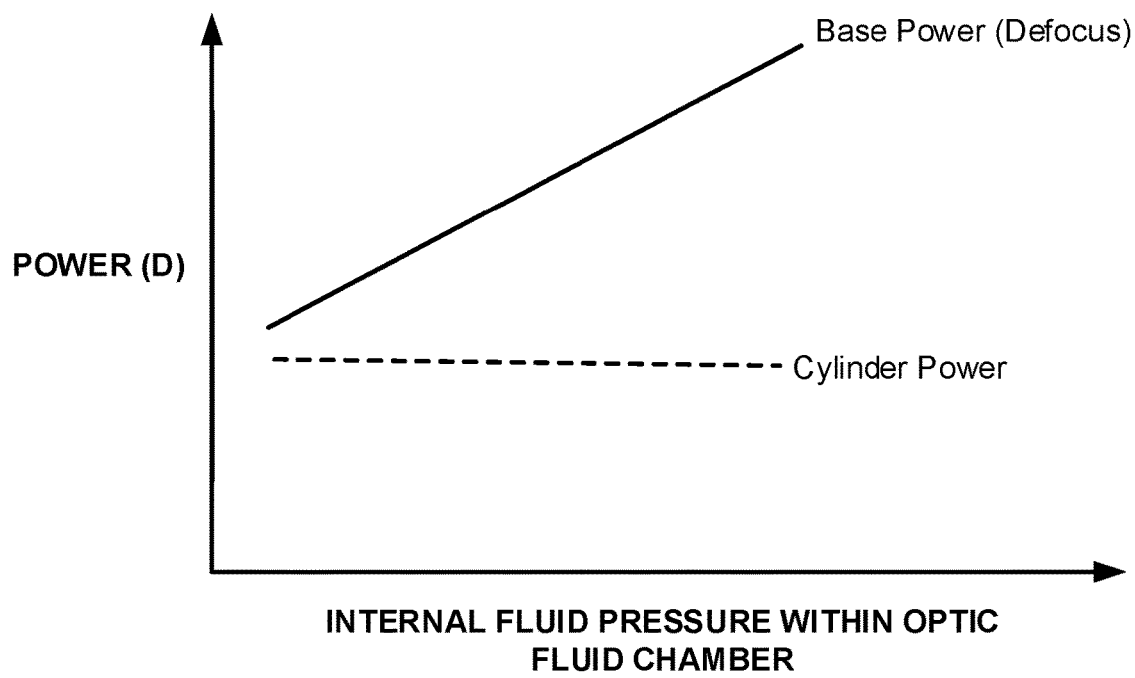
FIG. 5 is a graph illustrating changes in certain powers of the toric accommodating intraocular lens as a function of internal fluid pressure within the optic fluid chamber of the lens.

FIG. 5 is a graph illustrating changes in certain powers of the toric AIOL 100 as a function of internal fluid pressure within the optic fluid chamber 110. As shown in FIG. 5, the base power of the toric AIOL 100 (or the ability of the toric AIOL 100 to address defocus aberration) is highly responsive to changes in fluid pressure within the fluid-filled optic fluid chamber 110. As the internal fluid pressure within the fluid-filled optic fluid chamber 110 increases, the base power of the toric AIOL 100 increases.

FIG. 5 also illustrates that the cylinder power of the toric AIOL 100 remains relatively unchanged and stable despite changes in fluid pressure within the fluid-filled optic fluid chamber 110. Moreover, the ability of the toric AIOL 100 to correct for spherical aberration also remains relatively unchanged despite changes in fluid pressure within the fluid-filled optic fluid chamber 110.

Figure 6:
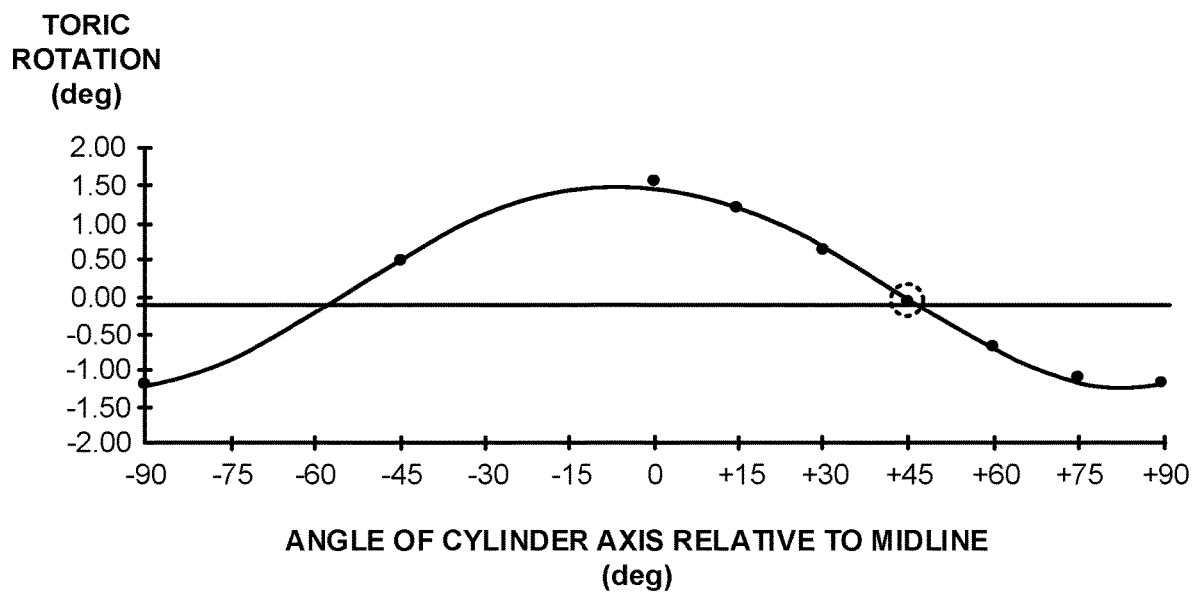
FIG. 6 is a graph illustrating cylinder stability in terms of amount of toric rotation as a function of the angle of cylinder axis relative to a midline of the intraocular lens.

FIG. 6 is a graph illustrating cylinder stability as a function of cylinder axis placement. Any changes in the cylinder orientation (expressed as the degree of "toric rotation" along the y-axis) were recorded for different versions of the toric AIOL 100 with different cylinder axis placement angles. All such versions of the toric AIOL 100 were subjected to axial loading and unloading using finite element analysis. As shown in FIG. 6, all cylinder axis (i.e., flat meridian) placement angles are measured as clockwise rotational angles with respect to the midline 154 of the toric AIOL 100. The preferred cylinder axis orientation (i.e., cylinder axis placement angle) is one that maintains cylinder stability throughout all phases of lens accommodation and disaccommodation.

As can be seen in FIG. 6, the toric AIOL 100 having a cylinder axis placement angle of +45 degrees relative to the midline exhibited almost 0 degree of toric rotation (or almost no change in cylinder orientation) despite being subjected to axial loading and unloading.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A toric accommodating intraocular lens, comprising:
   an optic portion comprising an anterior element having an anterior optical surface, a posterior element having a posterior optical surface, and a fluid-filled optic fluid chamber defined therebetween;
   a first haptic coupled to the optic portion at a first haptic-optic interface; and
   a second haptic coupled to the optic portion at a second haptic-optic interface diametrically opposed to the first haptic-optic interface,
      wherein the posterior optical surface is shaped such that a radius of curvature of the posterior optical surface differs along different optical surface meridians,
      wherein the posterior optical surface comprises a flat meridian and a steep meridian oriented substantially perpendicular to the flat meridian, and wherein the radius of curvature is the least along the steep meridian and the radius of curvature is the greatest along the flat meridian, and
      wherein the flat meridian is oriented at an oblique angle with respect to a midline substantially bisecting the first haptic-optic interface and the second haptic-optic interface.

2. The toric accommodating intraocular lens of claim 1, wherein the radius of curvature of the posterior optical surface varies periodically around the posterior optical surface.

3. The toric accommodating intraocular lens of claim 1, wherein the posterior element further comprises a posterior inner surface that is rotationally symmetric.

4. The toric accommodating intraocular lens of claim 3, wherein the posterior element has a posterior element thickness as measured from the posterior optical surface to the posterior inner surface, wherein the posterior element thickness varies periodically around the posterior element.

5. The toric accommodating intraocular lens of claim 1, wherein a base power of the optic portion is configured to change based on a pressure within the fluid-filled optic fluid chamber.

6. The toric accommodating intraocular lens of claim 5, wherein a cylinder power of the optic portion is configured to remain substantially unchanged throughout the change in base power of the optic portion in response to changes in the pressure within the fluid-filled optic fluid chamber.

7. The toric accommodating intraocular lens of claim 5, wherein a cylinder orientation of the optic portion is configured to remain substantially unchanged throughout the change in base power of the optic portion in response to changes in the pressure within the fluid-filled optic fluid chamber.

8. The toric accommodating intraocular lens of claim 1, wherein the oblique angle is a clockwise rotational angle between about 30 degrees and 60 degrees.

9. A toric accommodating intraocular lens, comprising:
   an optic portion comprising an anterior element having an anterior optical surface, a posterior element having a posterior optical surface, and a fluid-filled optic fluid chamber defined therebetween;
   wherein the optic portion comprises a first pair of fluid channels configured to place the fluid-filled optic fluid chamber in fluid communication with a haptic fluid chamber and a second pair of fluid channels configured to place the fluid-filled optic fluid chamber in fluid communication with another haptic fluid chamber,
   wherein the posterior optical surface is shaped such that a radius of curvature of the posterior optical surface differs along different optical surface meridians,
   wherein the posterior optical surface comprises a flat meridian and a steep meridian oriented substantially perpendicular to the flat meridian,
   wherein the radius of curvature is the least along the steep meridian and the radius of curvature is the greatest along the flat meridian, and
   wherein the flat meridian is oriented at an oblique angle with respect to a midline extending in between the first pair of fluid channels and in between the second pair of fluid channels.

10. The toric accommodating intraocular lens of claim 9, wherein the radius of curvature of the posterior optical surface varies periodically around the posterior optical surface.

11. The toric accommodating intraocular lens of claim 9, wherein the posterior element further comprises a posterior inner surface that is rotationally symmetric, wherein the posterior element has a posterior element thickness as measured from the posterior optical surface to the posterior inner surface, wherein the posterior element thickness varies periodically around the posterior element.

12. The toric accommodating intraocular lens of claim 9, wherein a base power of the optic portion is configured to change based on a pressure within the fluid-filled optic fluid chamber.

13. The toric accommodating intraocular lens of claim 12, wherein a cylinder power of the optic portion is configured to remain substantially unchanged throughout the change in base power of the optic portion in response to changes in the pressure within the fluid-filled optic fluid chamber.

14. The toric accommodating intraocular lens of claim 12, wherein a cylinder orientation of the optic portion is configured to remain substantially unchanged throughout the change in base power of the optic portion in response to changes in the pressure within the fluid-filled optic fluid chamber.

15. A toric accommodating intraocular lens, comprising:
an optic portion comprising an external optical surface and a fluid-filled optic fluid chamber defined within the optic portion,
wherein a refractive dioptric power of the external optical surface is greatest along a steep meridian of the external optical surface and the refractive dioptric power of the external optical surface is least along a flat meridian of the external optical surface, and wherein another optical surface opposite the external optical surface is an aspherical surface, and
wherein the flat meridian is oriented at an oblique angle with respect to a midline substantially bisecting the optic portion.

16. The toric accommodating intraocular lens of claim 15, wherein a base power of the optic portion is configured to change based on a pressure within the fluid-filled optic fluid chamber.

17. The toric accommodating intraocular lens of claim 16, wherein the relative refractive dioptric power between the flat meridian and the steep meridian is configured to remain substantially unchanged throughout the change in the base power of the optic portion in response to changes in the pressure within the fluid-filled optic fluid chamber.

18. The toric accommodating intraocular lens of claim 16, wherein an orientation of the flat meridian is configured to remain substantially unchanged throughout the change in the base power of the optic portion in response to changes in the pressure within the fluid-filled optic fluid chamber.

19. The toric accommodating intraocular lens of claim 15, further comprising a first haptic coupled to the optic portion at a first haptic-optic interface and a second haptic coupled to the optic portion at a second haptic-optic interface diametrically opposed to the first haptic-optic interface, and wherein the midline substantially bisects the first haptic-optic interface and the second haptic-optic interface.

20. The toric accommodating intraocular lens of claim 15, wherein the optic portion comprises a first pair of fluid channels configured to place the fluid-filled optic fluid chamber in fluid communication with a haptic fluid chamber and a second pair of fluid channels configured to place the fluid-filled optic fluid chamber in fluid communication with another haptic fluid chamber, and wherein the midline extends in between the first pair of fluid channels and in between the second pair of fluid channels.

* * * * *